United States Patent
Gardner et al.

(10) Patent No.: US 11,607,346 B2
(45) Date of Patent: Mar. 21, 2023

(54) DRESSING FOR NEGATIVE PRESSURE WOUND THERAPY WITH FILTER

(71) Applicant: Smith & Nephew PLC, Watford (GB)

(72) Inventors: Benjamin Gardner, Hull (GB); Samuel John Mortimer, Kingston upon Hull (GB); Neill John Rawson, Doncaster (GB)

(73) Assignee: Smith & Nephew PLC, Watford (GB)

( * ) Notice: Subject to any disclaimer, the term of this patent is extended or adjusted under 35 U.S.C. 154(b) by 6 days.

(21) Appl. No.: 16/759,988

(22) PCT Filed: Oct. 25, 2018

(86) PCT No.: PCT/EP2018/079329
§ 371 (c)(1),
(2) Date: Apr. 28, 2020

(87) PCT Pub. No.: WO2019/086330
PCT Pub. Date: May 9, 2019

(65) Prior Publication Data
US 2020/0282115 A1    Sep. 10, 2020

(30) Foreign Application Priority Data
Nov. 1, 2017 (GB) ..................................... 1718014

(51) Int. Cl.
*A61M 1/00* (2006.01)
*A61F 13/00* (2006.01)
*A61F 13/02* (2006.01)

(52) U.S. Cl.
CPC .... *A61F 13/0216* (2013.01); *A61F 13/00068* (2013.01); *A61F 13/0206* (2013.01);
(Continued)

(58) Field of Classification Search
CPC ............ A61F 13/00068; A61F 13/0206; A61F 13/0216; A61F 13/0209; A61F 13/022;
(Continued)

(56) References Cited

U.S. PATENT DOCUMENTS

| 3,568,675 A | 3/1971 | Harvey |
| 3,943,734 A | 3/1976 | Fleissner |

(Continued)

FOREIGN PATENT DOCUMENTS

| EP | 0982015 B1 | 8/2006 |
| EP | 2529766 A3 | 12/2012 |

(Continued)

OTHER PUBLICATIONS

International Preliminary Report on Patentability for Application No. PCT/EP2018/079329, dated May 14, 2020, 8 pages.

(Continued)

*Primary Examiner* — Erich G Herbermann
*Assistant Examiner* — Seth Han
(74) *Attorney, Agent, or Firm* — Knobbe, Martens Olson & Bear, LLP

(57) ABSTRACT

Disclosed herein are several embodiments of a wound treatment apparatus employing a wound dressing for negative pressure wound therapy and methods of using the same. Some embodiments are directed to improved wound dressing to be applied to a wound site, for example a wound dressing including a three-dimensional filter element, and methods of using the same.

22 Claims, 17 Drawing Sheets

(52) U.S. Cl.
CPC .............. *A61M 1/912* (2021.05); *A61M 1/784* (2021.05); *A61M 1/913* (2021.05); *A61M 2205/75* (2013.01); *A61M 2205/7518* (2013.01); *A61M 2205/7536* (2013.01)

(58) Field of Classification Search
CPC ............ A61F 13/0223; A61F 13/0226; A61M 2205/7518; A61M 2205/7536; A61M 1/784; A61M 205/75; A61M 1/86; A61M 1/90; A61M 2205/75; A61M 2205/7563; A61M 2205/7527; A61M 2205/7554; A61M 1/91; A61M 1/912; A61M 1/913
USPC ........................................................ 604/319
See application file for complete search history.

(56) References Cited

U.S. PATENT DOCUMENTS

| | | | |
|---|---|---|---|
| 4,605,399 A | 8/1986 | Weston et al. | |
| 4,921,492 A | 5/1990 | Schultz et al. | |
| 4,969,880 A | 11/1990 | Zamierowski | |
| 5,056,510 A | 10/1991 | Gilman | |
| 5,100,396 A | 3/1992 | Zamierowski | |
| 5,106,362 A | 4/1992 | Gilman | |
| 5,180,375 A | 1/1993 | Feibus | |
| 5,261,893 A | 11/1993 | Zamierowski | |
| 5,358,492 A | 10/1994 | Feibus | |
| 5,527,293 A | 6/1996 | Zamierowski | |
| 5,599,289 A | 2/1997 | Castellana | |
| 5,618,556 A | 4/1997 | Johns et al. | |
| 5,645,081 A | 7/1997 | Argenta et al. | |
| 5,678,564 A | 10/1997 | Lawrence et al. | |
| 5,701,917 A | 12/1997 | Khouri | |
| 5,795,584 A | 8/1998 | Totakura et al. | |
| 6,071,267 A | 6/2000 | Zamierowski | |
| 6,209,541 B1* | 4/2001 | Wallace | A61M 16/1055 128/200.24 |
| 6,345,623 B1 | 2/2002 | Heaton et al. | |
| 6,458,109 B1 | 10/2002 | Henley et al. | |
| 6,626,891 B2 | 9/2003 | Ohmstede | |
| 6,648,862 B2 | 11/2003 | Watson | |
| 6,685,681 B2 | 2/2004 | Lockwood et al. | |
| 6,752,794 B2 | 6/2004 | Lockwood et al. | |
| 6,755,807 B2 | 6/2004 | Risk, Jr. et al. | |
| 6,855,135 B2 | 2/2005 | Lockwood et al. | |
| 6,936,037 B2 | 8/2005 | Bubb et al. | |
| 6,951,553 B2 | 10/2005 | Bubb et al. | |
| D515,701 S | 2/2006 | Horhota et al. | |
| 7,004,915 B2 | 2/2006 | Boynton et al. | |
| 7,070,584 B2 | 7/2006 | Johnson et al. | |
| 7,108,683 B2 | 9/2006 | Zamierowski | |
| 7,216,651 B2 | 5/2007 | Argenta et al. | |
| 7,279,612 B1 | 10/2007 | Heaton et al. | |
| 7,338,482 B2 | 3/2008 | Lockwood et al. | |
| 7,381,859 B2 | 6/2008 | Hunt et al. | |
| 7,438,705 B2 | 10/2008 | Karpowicz et al. | |
| 7,485,112 B2 | 2/2009 | Karpowicz et al. | |
| 7,503,910 B2 | 3/2009 | Adahan | |
| 7,531,711 B2 | 5/2009 | Sigurjonsson et al. | |
| 7,534,927 B2 | 5/2009 | Lockwood et al. | |
| 7,569,742 B2 | 8/2009 | Haggstrom et al. | |
| 7,611,500 B1 | 11/2009 | Lina et al. | |
| 7,645,269 B2 | 1/2010 | Zamierowski | |
| 7,651,484 B2 | 1/2010 | Heaton et al. | |
| 7,670,323 B2 | 3/2010 | Hunt et al. | |
| 7,678,102 B1 | 3/2010 | Heaton | |
| 7,686,785 B2 | 3/2010 | Boehringer et al. | |
| 7,699,831 B2 | 4/2010 | Bengtson et al. | |
| 7,862,718 B2 | 1/2011 | Doyen et al. | |
| 7,880,050 B2 | 2/2011 | Robinson et al. | |
| 7,896,864 B2 | 3/2011 | Lockwood et al. | |
| 7,922,703 B2 | 4/2011 | Riesinger | |
| 7,942,866 B2 | 5/2011 | Radl et al. | |
| 7,951,124 B2 | 5/2011 | Boehringer et al. | |
| 7,976,519 B2 | 7/2011 | Bubb et al. | |
| 7,981,098 B2 | 7/2011 | Boehringer et al. | |
| 8,021,347 B2 | 9/2011 | Vitaris et al. | |
| 8,083,712 B2 | 12/2011 | Biggie et al. | |
| 8,105,295 B2 | 1/2012 | Blott et al. | |
| 8,129,580 B2 | 3/2012 | Wilkes et al. | |
| 8,133,211 B2 | 3/2012 | Cavanaugh, II et al. | |
| 8,147,468 B2 | 4/2012 | Barta et al. | |
| 8,152,785 B2 | 4/2012 | Vitaris | |
| 8,158,844 B2 | 4/2012 | McNeil | |
| 8,162,907 B2 | 4/2012 | Heagle | |
| 8,168,848 B2 | 5/2012 | Lockwood et al. | |
| 8,187,237 B2 | 5/2012 | Seegert | |
| 8,188,331 B2 | 5/2012 | Barta et al. | |
| 8,192,409 B2 | 6/2012 | Hardman et al. | |
| 8,202,261 B2 | 6/2012 | Kazala, Jr. et al. | |
| 8,241,261 B2 | 8/2012 | Randolph et al. | |
| 8,246,606 B2 | 8/2012 | Stevenson et al. | |
| 8,267,908 B2 | 9/2012 | Coulthard | |
| 8,372,049 B2 | 2/2013 | Jaeb et al. | |
| 8,376,972 B2 | 2/2013 | Fleischmann | |
| 8,382,731 B2 | 2/2013 | Johannison | |
| 8,399,730 B2 | 3/2013 | Kazala, Jr. et al. | |
| 8,409,170 B2 | 4/2013 | Locke et al. | |
| 8,506,554 B2 | 8/2013 | Adahan | |
| 8,513,481 B2 | 8/2013 | Gergely et al. | |
| 8,545,466 B2 | 10/2013 | Andresen et al. | |
| 8,734,410 B2 | 5/2014 | Hall et al. | |
| 8,771,244 B2 | 7/2014 | Eckstein et al. | |
| 8,784,392 B2 | 7/2014 | Vess et al. | |
| 8,801,685 B2 | 8/2014 | Armstrong et al. | |
| 8,814,842 B2 | 8/2014 | Coulthard et al. | |
| 8,905,985 B2 | 12/2014 | Allen et al. | |
| 9,033,942 B2 | 5/2015 | Vess | |
| 9,050,398 B2 | 6/2015 | Armstrong et al. | |
| 9,061,095 B2 | 6/2015 | Adie et al. | |
| D746,435 S | 12/2015 | Armstrong et al. | |
| RE45,864 E | 1/2016 | Peron | |
| 9,227,000 B2 | 1/2016 | Fink et al. | |
| D755,980 S | 5/2016 | Jakobsen et al. | |
| 9,364,647 B1* | 6/2016 | Beckman | A61M 27/006 |
| 9,474,654 B2 | 10/2016 | Heagle et al. | |
| RE46,289 E | 1/2017 | Peron | |
| 9,539,373 B2 | 1/2017 | Jones et al. | |
| 9,681,993 B2 | 6/2017 | Wu et al. | |
| 9,877,872 B2 | 1/2018 | Mumby et al. | |
| 9,907,703 B2 | 3/2018 | Allen et al. | |
| 10,076,594 B2 | 9/2018 | Collinson et al. | |
| 2003/0060750 A1 | 3/2003 | Van Der Linden | |
| 2005/0119607 A1 | 6/2005 | Van Der Linden et al. | |
| 2005/0137539 A1 | 6/2005 | Biggie et al. | |
| 2007/0057389 A1 | 3/2007 | Davis et al. | |
| 2007/0265585 A1 | 11/2007 | Joshi et al. | |
| 2008/0033325 A1 | 2/2008 | Van der Hulst | |
| 2009/0293887 A1 | 12/2009 | Wilkes et al. | |
| 2009/0299251 A1 | 12/2009 | Buan | |
| 2009/0299257 A1 | 12/2009 | Long et al. | |
| 2009/0299308 A1 | 12/2009 | Kazala, Jr. et al. | |
| 2009/0299340 A1 | 12/2009 | Kazala, Jr. et al. | |
| 2010/0030178 A1 | 2/2010 | Macmeccan et al. | |
| 2010/0069850 A1 | 3/2010 | Fabo | |
| 2010/0069886 A1 | 3/2010 | Wilkes | |
| 2010/0125259 A1 | 5/2010 | Olson | |
| 2010/0160901 A1 | 6/2010 | Hu et al. | |
| 2011/0028918 A1 | 2/2011 | Hartwell | |
| 2011/0054421 A1 | 3/2011 | Hartwell | |
| 2011/0071483 A1 | 3/2011 | Gordon et al. | |
| 2011/0130712 A1 | 6/2011 | Topaz | |
| 2011/0172615 A2 | 7/2011 | Greener | |
| 2012/0302976 A1 | 11/2012 | Locke et al. | |
| 2013/0030395 A1 | 1/2013 | Croizat et al. | |
| 2013/0123723 A1* | 5/2013 | Tout | A61M 1/90 604/319 |
| 2013/0172835 A1 | 7/2013 | Braga et al. | |
| 2013/0190706 A1 | 7/2013 | Kleiner | |
| 2014/0121615 A1 | 5/2014 | Locke et al. | |
| 2014/0163490 A1* | 6/2014 | Locke | A61F 13/0206 604/319 |
| 2014/0194835 A1 | 7/2014 | Ehlert | |
| 2014/0228786 A1 | 8/2014 | Croizat et al. | |

(56) References Cited

U.S. PATENT DOCUMENTS

| | | | |
|---|---|---|---|
| 2014/0296805 A1 | 10/2014 | Arthur et al. | |
| 2014/0343520 A1 | 11/2014 | Bennett et al. | |
| 2014/0350494 A1 | 11/2014 | Hartwell et al. | |
| 2015/0157784 A1 | 6/2015 | Santora et al. | |
| 2015/0190286 A1 | 7/2015 | Allen | |
| 2015/0231314 A1* | 8/2015 | Robinson | A61M 1/915 604/319 |
| 2015/0320604 A1* | 11/2015 | Adie | A61M 1/962 604/319 |
| 2016/0144084 A1 | 5/2016 | Collinson et al. | |
| 2016/0339158 A1* | 11/2016 | Collinson | A61M 1/86 |
| 2018/0042521 A1 | 2/2018 | Ryu et al. | |

FOREIGN PATENT DOCUMENTS

| | | | |
|---|---|---|---|
| EP | 2628500 B1 | 5/2014 | |
| WO | WO-0061206 A1 | 10/2000 | |
| WO | WO-2004018020 A1 | 3/2004 | |
| WO | WO-2005016179 A2 | 2/2005 | |
| WO | WO-2005061025 A1 | 7/2005 | |
| WO | WO-2007006306 A2 | 1/2007 | |
| WO | WO-2007016590 A2 | 2/2007 | |
| WO | WO-2007019038 A2 | 2/2007 | |
| WO | WO-2007085396 A1 | 8/2007 | |
| WO | WO-2007095180 A2 | 8/2007 | |
| WO | WO-2007106590 A2 | 9/2007 | |
| WO | WO-2007106591 A2 | 9/2007 | |
| WO | WO-2008008032 A1 | 1/2008 | |
| WO | WO-2008012278 A1 | 1/2008 | |
| WO | WO-2008043067 A2 | 4/2008 | |
| WO | WO-2008131895 A1 | 11/2008 | |
| WO | WO-2008135997 A2 | 11/2008 | |
| WO | WO-2008141470 A1 | 11/2008 | |
| WO | WO-2009068665 A1 | 6/2009 | |
| WO | WO-2009086580 A1 | 7/2009 | |
| WO | WO-2009088925 A1 | 7/2009 | |
| WO | WO-2009137194 A2 | 11/2009 | |
| WO | WO-2009140376 A1 | 11/2009 | |
| WO | WO-2010078166 A2 | 7/2010 | |
| WO | WO-2010120470 A1 | 10/2010 | |
| WO | WO-2011049562 A1 | 4/2011 | |
| WO | WO-2011100851 A1 | 8/2011 | |
| WO | WO-2012142002 A1 | 10/2012 | |
| WO | WO-2013016239 A1 | 1/2013 | |
| WO | WO-2013019438 A1 | 2/2013 | |
| WO | WO-2013043972 A1 | 3/2013 | |
| WO | WO-2013123005 A1 | 8/2013 | |
| WO | WO-2014022400 A1 * | 2/2014 | ....... A61F 13/00068 |
| WO | WO-2014043238 A3 | 9/2014 | |
| WO | WO-2014158526 A1 | 10/2014 | |
| WO | WO-2016174048 A1 | 11/2016 | |
| WO | WO-2017068364 A1 | 4/2017 | |
| WO | WO-2017087163 A1 | 5/2017 | |
| WO | WO-2017097834 A1 | 6/2017 | |
| WO | WO-2017186771 A1 | 11/2017 | |

OTHER PUBLICATIONS

International Search Report and Written Opinion for Application No. PCT/EP2018/079329, dated Feb. 1, 2019, 9 pages (PT-5134-WO-PCT).

The Wayback Machine, "Comfort advantages with AirX™," retrieved from http://web.archive.org/web/20090121000205/http://www.airx.eu:80/content/view/2/3/lang,en/, on Jan. 21, 2009, 1 page.

The Wayback Machine, "Moisture-Transporting Material," retrieved from http://web.archive.org/web/20090121001036/http://www.airx.eu/content/view/1/14/lang,en/, on Jan. 21, 2009, 1 page.

* cited by examiner

DRESSING FOR NEGATIVE PRESSURE WOUND THERAPY WITH FILTER

RELATED APPLICATIONS

This application claims priority to U. K. Provisional Application No. 1718014.2, filed Nov. 1, 2017, entitled "DRESSING FOR NEGATIVE PRESSURE WOUND THERAPY WITH FILTER," the entirety of which is hereby incorporated by reference.

BACKGROUND

Field of the Invention

Embodiments of the present invention relate generally to the treatment of wounds using negative pressure wound therapy and more specifically to wound treatment apparatuses including a wound dressing and a fluidic connector for use therewith.

Description of the Related Art

The treatment of open or chronic wounds that are too large to spontaneously close or otherwise fail to heal by means of applying negative pressure to the site of the wound is well known in the art. Negative pressure wound therapy (NPWT) systems currently known in the art commonly involve placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines bacteria. However, further improvements in NPWT are needed to fully realize the benefits of treatment.

Many different types of wound dressings are known for aiding in NPWT systems. These different types of wound dressings include many different types of materials and layers, for example, gauze, pads, foam pads or multi-layer wound dressings. One example of a multi-layer wound dressing is the PICO dressing, available from Smith & Nephew, which includes a superabsorbent layer beneath a backing layer to provide a canister-less system for treating a wound with NPWT. The wound dressing may be sealed to a suction port providing connection to a length of tubing, which may be used to pump fluid out of the dressing and/or to transmit negative pressure from a pump to the wound dressing.

To provide a canister-less system for treating a wound with negative pressure, a filter to prevent wound fluid from escaping a wound dressing or a suction port and entering a pump, may be required to be included in the wound dressing or the suction port. At the same time, it would desirable that such filter allows uninterrupted air flow such that the negative pressure from a pump is transmitted to the wound site. However, accumulation of wound fluid under the filter, especially under the negative pressure, may obstruct air flow through filters, and thus compromise the benefit of NPWT. Accordingly, there is a need to provide for an improved apparatus, method, and system for filter for the treatment and closure of wounds.

SUMMARY

Embodiments of the present disclosure relate to wound treatment apparatuses, wound treatment devices and methods of treating a wound. In some embodiments of the wound treatment apparatuses described herein, a three-dimensional filter element is utilized with a wound dressing comprising an absorbent material. Wound treatment apparatuses may also comprise a fluidic connector that may be used in combination with the three-dimensional filter element and the wound dressing described herein. In some embodiments, a three-dimensional filter element is incorporated into a fluidic connector so that the fluidic connector and the three-dimensional filter are part of an integral or integrated fluidic connector structure that delivers negative pressure to the wound dressing and prevents wound exudate from escaping from the wound dressing. These and other embodiments as described herein are directed to overcoming particular challenges involved with preventing wound exudate or wound fluid from escaping a wound dressing under negative pressure.

According to some embodiments there is provided a wound treatment apparatus comprising:
a wound dressing comprising:
a cover layer comprising an aperture; and
an absorbent layer comprising a recess extending vertically through a thickness of the absorbent layer at least partially, the absorbent layer positioned beneath the cover layer; and
a fluidic connector configured to provide negative pressure to the wound dressing through the aperture in the cover layer; and
a three-dimensional filter element configured to prevent wound exudate from exiting the wound dressing through the aperture of the cover layer when negative pressure is provided to the wound dressing, wherein the three-dimensional filter extends vertically along at least a portion of the thickness of the absorbent layer within the recess.

The wound treatment apparatus of the preceding paragraph or in other embodiments can include one or more of the following features. In some embodiments, the three-dimensional filter element spans the aperture in the cover layer. The recess may be a through-hole which extends through the entire thickness of the absorbent layer. The three-dimensional filter element may be at least partially cylindrically shaped or cuboid-shaped. The three-dimensional filter element may have a height greater than 3 mm. In some embodiments, the three-dimensional filter element further comprises a filter layer. The filter layer may be oleophobic. In some embodiments, the three-dimensional filter element further comprises a spacer core, wherein the spacer core is at least partially enclosed by the filter layer. The spacer core may comprise cellulose. In some embodiments, the three-dimensional filter element is adhered to the fluidic connector. The three-dimensional filter element may extend below the fluidic connector. In some embodiment, the wound dressing further comprises a wound contact layer, a transmission layer, and/or a source of negative pressure.

According to some embodiments there is provided a wound treatment apparatus comprising:
a wound dressing comprising:
a cover layer comprising an aperture; and
an absorbent layer positioned beneath the cover layer, the absorbent layer having a thickness;
a fluidic connector configured to provide negative pressure to the wound dressing through the aperture in the cover layer; and a three-dimensional filter element configured to prevent wound exudate from exiting the wound dressing through the aperture of the cover layer when negative pressure is provided to the wound dressing.

The wound treatment apparatus of the preceding paragraph or in other embodiments can include one or more of the following features. In some embodiments, the three-dimensional filter element extends along at least a portion of the thickness of the absorbent layer. The absorbent layer may comprise a recess extending vertically through a thickness of the absorbent layer at least partially, and three-dimensional filter element may extend vertically along at least a portion of the thickness of the absorbent layer within the recess. In some embodiments, the three-dimensional filter element may be above the absorbent layer. The three-dimensional filter element may spans the aperture in the cover layer. The three-dimensional filter element may be at least partially cylindrically shaped or cuboid-shaped. The three-dimensional filter element may have a height greater than 3 mm. In some embodiments, the three-dimensional filter element further comprises a filter layer. The filter layer may be oleophobic. In some embodiments, the three-dimensional filter element further comprises a spacer core, wherein the spacer core is at least partially enclosed by the filter layer. The spacer core may comprise cellulose. In some embodiments, the three-dimensional filter element is adhered to the fluidic connector. The three-dimensional filter element may extend below the fluidic connector. In some embodiment, the wound dressing further comprises a wound contact layer, a transmission layer and/or a source of negative pressure.

Other embodiments of an apparatus for use with wound treatment, devices, kits and associated methods are described below.

BRIEF DESCRIPTION OF THE DRAWINGS

Other features and advantages of the present invention will be apparent from the following detailed description of the invention, taken in conjunction with the accompanying drawings of which.

DETAILED DESCRIPTION

Preferred embodiments disclosed herein relate to wound therapy for a human or animal body. Therefore, any reference to a wound herein can refer to a wound on a human or animal body, and any reference to a body herein can refer to a human or animal body. The term "wound" as used herein, in addition to having its broad ordinary meaning, includes any body part of a patient that may be treated using negative pressure. Wounds include, but are not limited to, open wounds, incisions, lacerations, abrasions, contusions, burns, diabetic ulcers, pressure ulcers, stoma, surgical wounds, trauma and venous ulcers or the like. Treatment of such wounds can be performed using negative pressure wound therapy, wherein a reduced or negative pressure can be applied to the wound to facilitate and promote healing of the wound. It will also be appreciated that the fluidic connector and methods as disclosed herein may be applied to other parts of the body, and are not necessarily limited to treatment of wounds.

Certain embodiments of this application related to a wound treatment apparatus employing a wound dressing and a fluidic connector, and to methods of using the same. Certain embodiments of this application relate to a fluidic connector and methods of using the same.

Figure 1A:
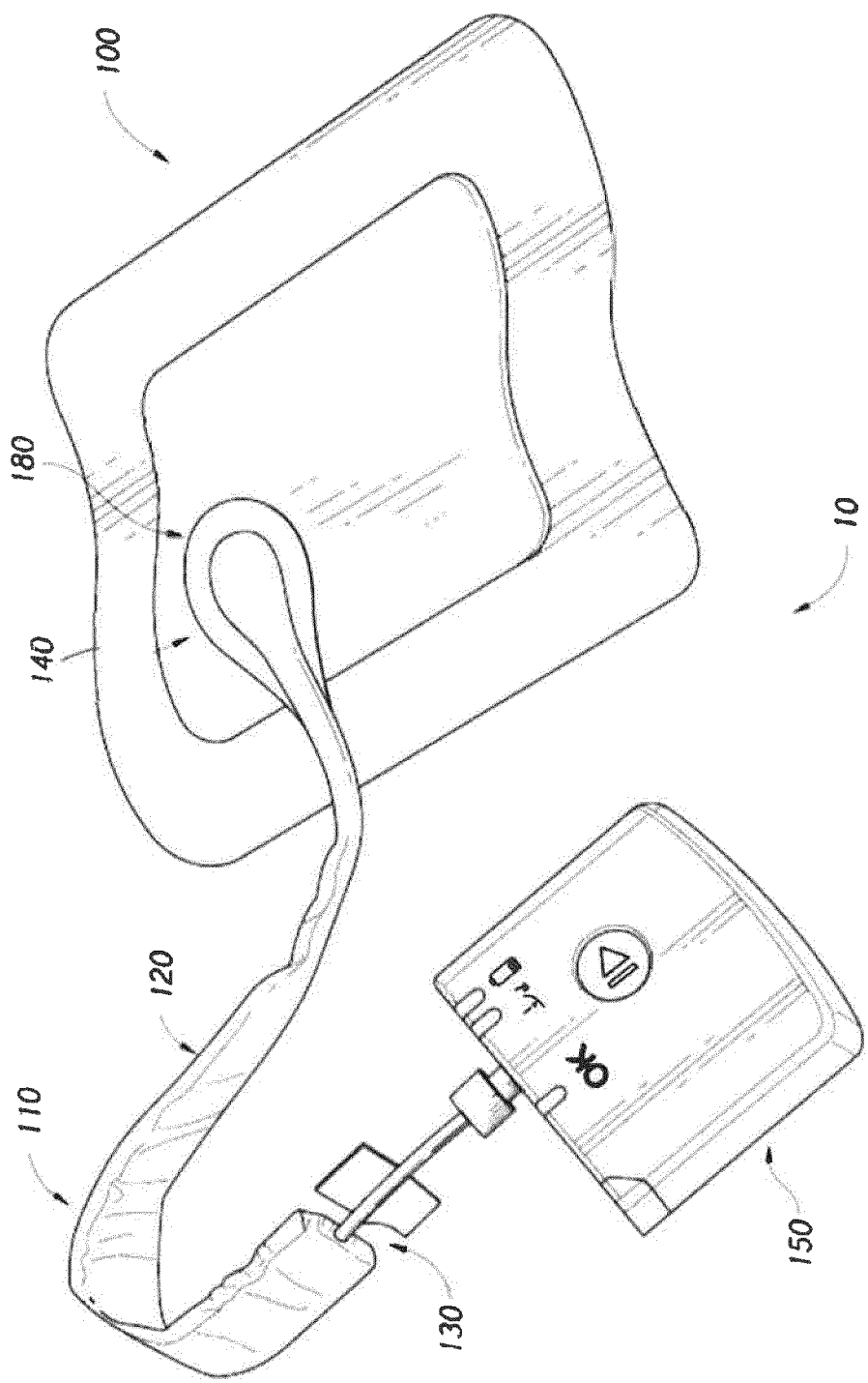
FIG. 1A illustrates an embodiment of a negative pressure wound treatment system employing a flexible fluidic connector and a wound dressing capable of absorbing and storing wound exudate.
Figure 1B:
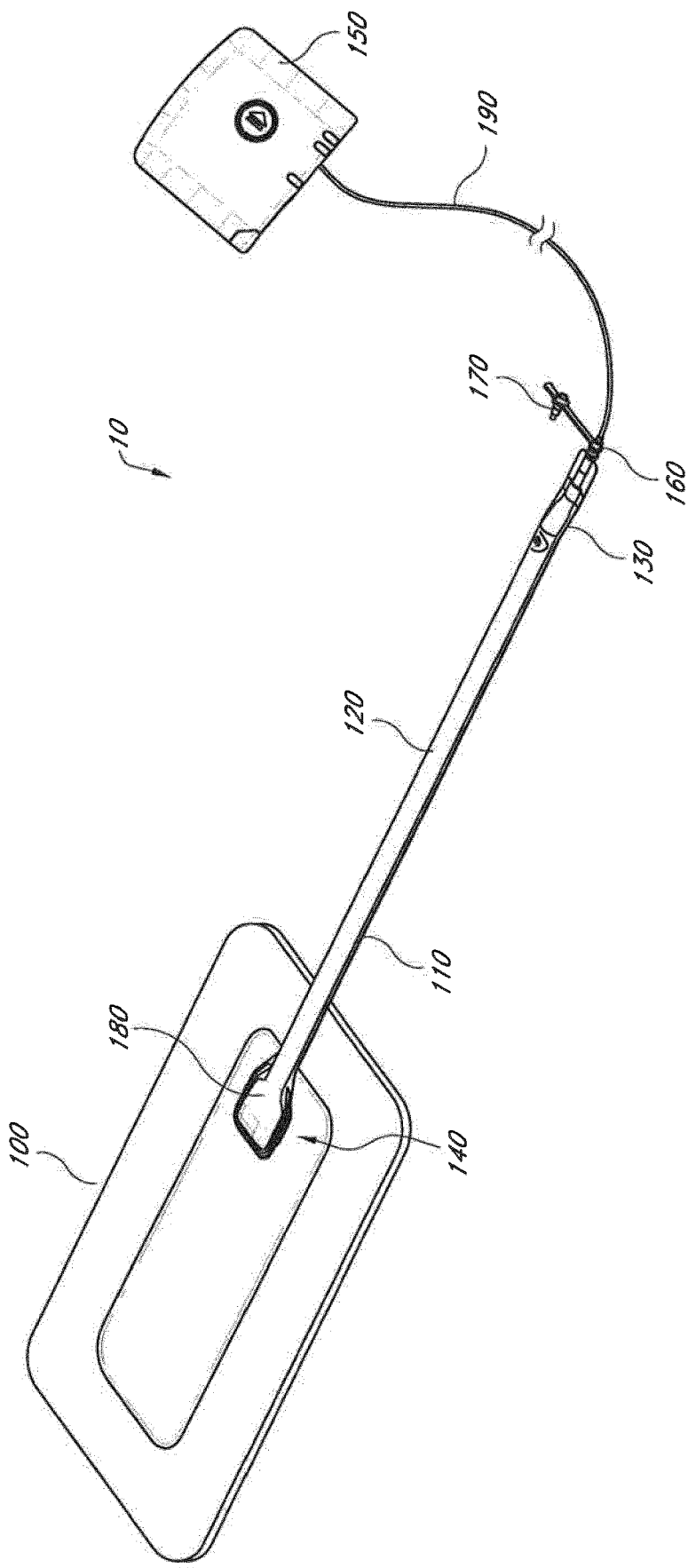
FIG. 1B illustrates an embodiment of a negative pressure wound treatment system employing a flexible fluidic connector and a wound dressing capable of absorbing and storing wound exudate.

FIGS. 1A-B illustrate embodiments of a negative pressure wound treatment system 10 employing a wound dressing 100 in conjunction with a fluidic connector 110. Here, the fluidic connector 110 may comprise an elongate conduit, more preferably a bridge 120 having a proximal end 130 and a distal end 140, and an applicator 180 at the distal end 140 of the bridge 120. An optional coupling 160 is preferably disposed at the proximal end 130 of the bridge 120. A cap 170 may be provided with the system (and can in some cases, as illustrated, be attached to the coupling 160). The cap 170 can be useful in preventing fluids from leaking out of the proximal end 130. The system 10 may include a source of negative pressure such as a pump or negative pressure unit 150 capable of supplying negative pressure. The pump may comprise a canister or other container for the storage of wound exudates and other fluids that may be removed from the wound. A canister or container may also be provided separate from the pump. In some embodiments, such as illustrated in FIGS. 1A-1B, the pump 150 can be a canisterless pump such as the PICO™ pump, as sold by Smith & Nephew. The pump 150 may be connected to the coupling 160 via a tube 190, or the pump 150 may be connected directly to the coupling 160 or directly to the bridge 120. In use, the dressing 100 is placed over a suitably-prepared wound, which may in some cases be filled with a wound packing material such as foam or gauze. The applicator 180 of the fluidic connector 110 has a sealing surface that is placed over an aperture in the dressing 100 and is sealed to the top surface of the dressing 100. Either before, during, or after connection of the fluidic connector 110 to the dressing 100, the pump 150 is connected via the tube 190 to the coupling 160, or is connected directly to the coupling 160 or to the bridge 120. The pump is then activated, thereby supplying negative pressure to the wound. Application of negative pressure may be applied until a desired level of healing of the wound is achieved.

Figure 2A:
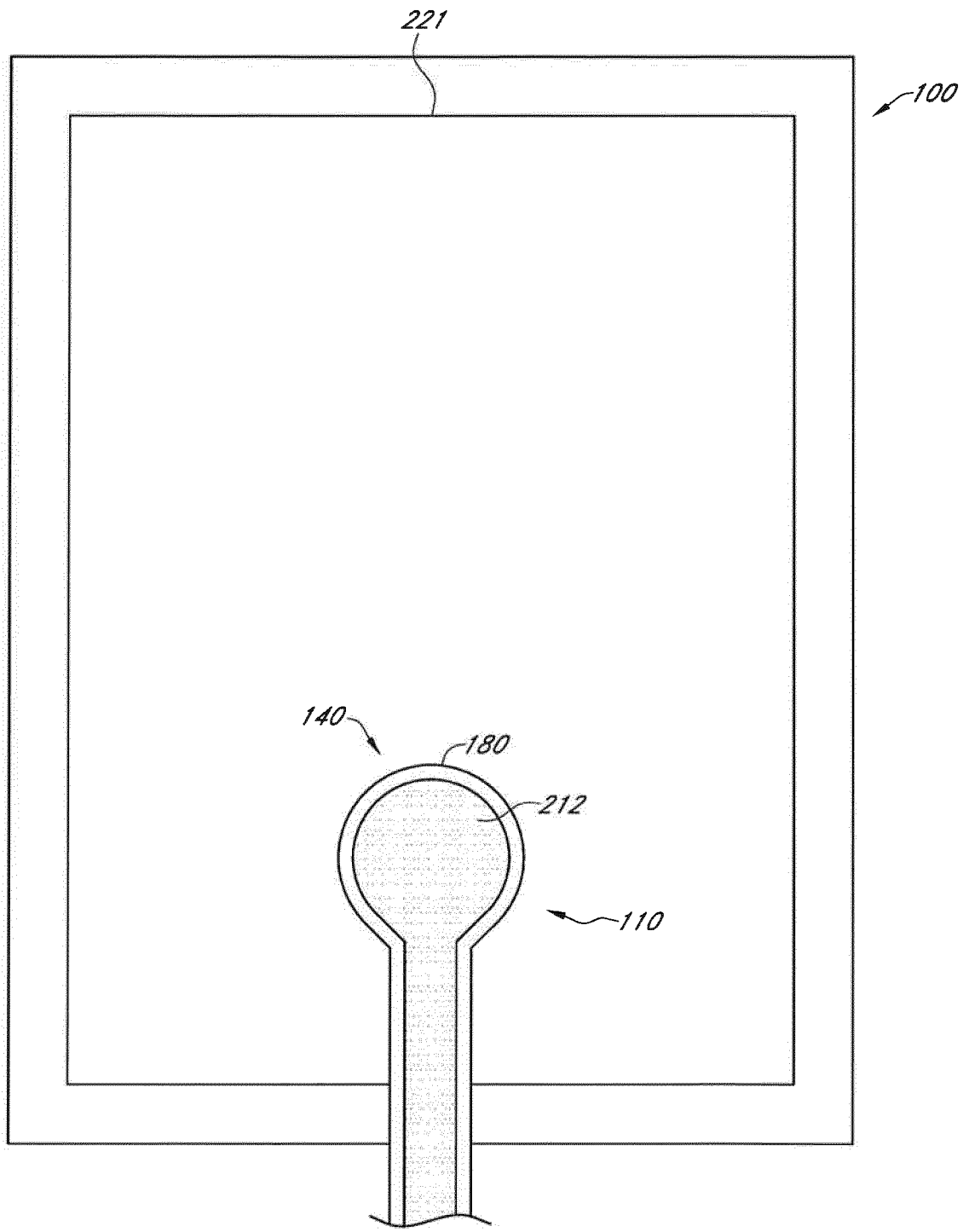
FIG. 2A illustrates an embodiment of a negative pressure wound treatment system employing a flexible fluidic connector and a wound dressing capable of absorbing and storing wound exudate.
Figure 2B:
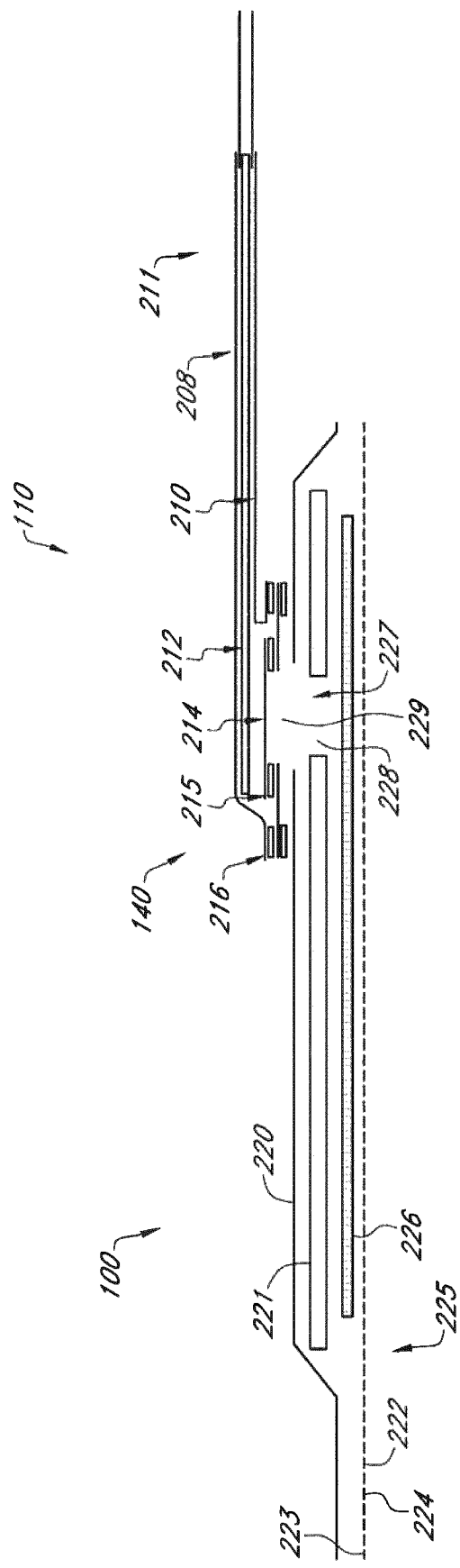
FIG. 2B illustrates a cross section of an embodiment of a fluidic connector connected to a wound dressing.

With reference initially to FIGS. 2A-B, treatment of a wound with negative pressure in certain embodiments of the application uses a wound dressing 100 capable of absorbing and storing wound exudate in conjunction with a flexible fluidic connector 110. In some embodiments, the wound dressing 100 may be substantially similar to wound dressings and have the same or similar components as those described throughout International Patent Publication WO2013175306, WO2014020440, WO2014020443 and U.S. Publication No. 2011/0282309 A1, which are incorporated by reference in their entireties. In other embodiments (not shown), the wound dressing may simply comprise one or more backing layers configured to form a sealed chamber over the wound site. In some embodiments, it may be preferable for the wound site to be filled partially or completely with a wound packing material. This wound packing material is optional, but may be desirable in certain wounds, for example deeper wounds. The wound packing material can be used in addition to the wound dressing 100. The wound packing material generally may comprise a porous and conformable material, for example foam (including reticulated foams), and gauze. Preferably, the wound packing material is sized or shaped to fit within the wound site so as to fill any empty spaces. The wound dressing 100 may then be placed over the wound site and wound packing material overlying the wound site. When a wound packing material is used, once the wound dressing 100 is sealed over the wound site, negative pressure may be transmitted from a pump or other source of negative pressure through a flexible tubing via the fluidic connector 110 to the wound dressing 100, through the wound packing material, and finally to the wound site. This negative pressure draws wound exudate and other fluids or secretions away from the wound site.

As shown in FIG. 2A, the fluidic connector 110 preferably comprises an enlarged distal end, or head 140 that is in fluidic communication with the dressing 100 as will be described in further detail below. In one embodiment, the enlarged distal end has a round or circular shape. The head 140 is illustrated here as being positioned near an edge of the dressing 100, but may also be positioned at any location on the dressing. For example, some embodiments may provide for a centrally or off-centered location not on or near an edge or corner of the dressing 100. In some embodiments, the dressing 10 may comprise two or more fluidic connectors 110, each comprising one or more heads 140, in fluidic communication therewith. In a preferred embodiment, the head 140 may measure 30 mm along its widest edge. The head 140 forms at least in part the applicator 180, described above, that is configured to seal against a top surface of the wound dressing.

FIG. 2B illustrates a cross-section through a wound dressing 100 similar to the wound dressing 10 as shown in FIG. 1B and described in International Patent Publication WO2013175306, which is incorporated by reference in its entirety, along with fluidic connector 110. The wound dressing 100, which can alternatively be any wound dressing embodiment disclosed herein or any combination of features of any number of wound dressing embodiments disclosed herein, can be located over a wound site to be treated. The dressing 100 may be placed to as to form a sealed cavity over the wound site. In a preferred embodiment, the dressing 100 comprises a top or cover layer, or backing layer 220 attached to an optional wound contact layer 222, both of which are described in greater detail below. These two layers 220, 222 are preferably joined or sealed together so as to define an interior space or chamber. This interior space or chamber may comprise additional structures that may be adapted to distribute or transmit negative pressure, store wound exudate and other fluids removed from the wound, and other functions which will be explained in greater detail below. Examples of such structures, described below, include a transmission layer 226 and an absorbent layer 221.

As illustrated in FIG. 2B, the wound contact layer 222 can be a polyurethane layer or polyethylene layer or other flexible layer which is perforated, for example via a hot pin process, laser ablation process, ultrasound process or in some other way or otherwise made permeable to liquid and gas. The wound contact layer 222 has a lower surface 224 and an upper surface 223. The perforations 225 preferably comprise through holes in the wound contact layer 222 which enable fluid to flow through the layer 222. The wound contact layer 222 helps prevent tissue ingrowth into the other material of the wound dressing. Preferably, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 222 may help maintain the integrity of the entire dressing 100 while also creating an air tight seal around the absorbent pad in order to maintain negative pressure at the wound.

Some embodiments of the wound contact layer 222 may also act as a carrier for an optional lower and upper adhesive layer (not shown). For example, a lower pressure sensitive adhesive may be provided on the lower surface 224 of the wound dressing 100 whilst an upper pressure sensitive adhesive layer may be provided on the upper surface 223 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized, it may be helpful to adhere the wound dressing 100 to the skin around a wound site. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer 226 of porous material can be located above the wound contact layer 222. This porous layer, or transmission layer, 226 allows transmission of fluid including liquid and gas away from a wound site into upper layers of the wound dressing. In particular, the transmission layer 226 preferably ensures that an open air channel can be maintained to communicate negative pressure over the wound area even when the absorbent layer has absorbed substantial amounts of exudates. The layer 226 should preferably remain open under the typical pressures that will be applied during negative pressure wound therapy as described above, so that the whole wound site sees an equalized negative pressure. The layer 226 may be formed of a material having a three dimensional structure. For example, a knitted or woven spacer fabric (for example Baltex 7970 weft knitted polyester) or a non-woven fabric could be used.

In some embodiments, the transmission layer 226 comprises a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 10 denier flat polyester and a third layer formed sandwiched between these two layers which is a region defined by a knitted polyester viscose, cellulose or the like mono filament fiber. Other materials and other linear mass densities of fiber could of course be used.

Whilst reference is made throughout this disclosure to a monofilament fiber it will be appreciated that a multistrand alternative could of course be utilized. The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer 221 helps lock the liquid away or itself wicks the liquid onwards towards the cover layer where it can be transpired.

Preferably, to improve the liquid flow across the transmission layer 226 (that is to say perpendicular to the channel region formed between the top and bottom spacer layers, the 3D fabric may be treated with a dry cleaning agent (such as, but not limited to, Perchloro Ethylene) to help remove any manufacturing products such as mineral oils, fats and/or waxes used previously which might interfere with the hydrophilic capabilities of the transmission layer. In some embodiments, an additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

A layer 221 of absorbent material is provided above the transmission layer 226. The absorbent material, which comprise a foam or non-woven natural or synthetic material, and which may optionally comprise a super-absorbent material, forms a reservoir for fluid, particularly liquid, removed from the wound site. In some embodiments, the layer 10 may also aid in drawing fluids towards the backing layer 220.

The material of the absorbent layer 221 may also prevent liquid collected in the wound dressing 100 from flowing freely within the dressing, and preferably acts so as to contain any liquid collected within the dressing. The absorbent layer 221 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 221 may typically be manufactured from ALLEVYN™ foam, Freudenberg 114-224-4 and/or Chem-Posite™ 11C-450. In some embodiments, the absorbent layer 221 may comprise a composite comprising super-absorbent powder, fibrous material such as cellulose, and bonding fibers. In a preferred embodiment, the composite is an airlaid, thermally-bonded composite.

In some embodiments, the absorbent layer 221 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

An aperture, hole, or orifice 227 is preferably provided in the backing layer 220 to allow a negative pressure to be applied to the dressing 100. The fluidic connector 110 is preferably attached or sealed to the top of the backing layer 220 over the orifice 227 made into the dressing 100, and communicates negative pressure through the orifice 227. A length of tubing may be coupled at a first end to the fluidic connector 110 and at a second end to a pump unit (not shown) to allow fluids to be pumped out of the dressing. Where the fluidic connector is adhered to the top layer of the wound dressing, a length of tubing may be coupled at a first end of the fluidic connector such that the tubing, or conduit, extends away from the fluidic connector parallel or substantially to the top surface of the dressing. The fluidic connector 110 may be adhered and sealed to the backing layer 220 using an adhesive such as an acrylic, cyanoacrylate, epoxy, UV curable or hot melt adhesive. The fluidic connector 110 may be formed from a soft polymer, for example a polyethylene, a polyvinyl chloride, a silicone or polyurethane having a hardness of 30 to 90 on the Shore A scale. In some embodiments, the fluidic connector 110 may be made from a soft or conformable material.

Preferably the absorbent layer 221 includes at least one through hole 228 located so as to underlie the fluidic connector 110. The through hole 228 may in some embodiments be the same size as the opening 227 in the backing layer, or may be bigger or smaller. As illustrated in FIG. 2B a single through hole can be used to produce an opening underlying the fluidic connector 110. It will be appreciated that multiple openings could alternatively be utilized. Additionally should more than one port be utilized according to certain embodiments of the present disclosure one or multiple openings may be made in the absorbent layer and the obscuring layer in registration with each respective fluidic connector. Although not essential to certain embodiments of the present disclosure the use of through holes in the super-absorbent layer may provide a fluid flow pathway which remains unblocked in particular when the absorbent layer is near saturation.

The aperture or through-hole 228 is preferably provided in the absorbent layer 221 beneath the orifice 227 such that the orifice is connected directly to the transmission layer 226. This allows the negative pressure applied to the fluidic connector 110 to be communicated to the transmission layer 226 without passing through the absorbent layer 221. This ensures that the negative pressure applied to the wound site is not inhibited by the absorbent layer as it absorbs wound exudates. In other embodiments, no aperture may be provided in the absorbent layer 221, or alternatively a plurality of apertures underlying the orifice 227 may be provided. In further alternative embodiments, additional layers such as another transmission layer or an obscuring layer such as described in International Patent Publication WO2014020440 may be provided over the absorbent layer 221 and beneath the backing layer 220.

The backing layer 220 is preferably gas impermeable, but moisture vapor permeable, and can extend across the width of the wound dressing 100. The backing layer 220, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the backing layer 220 and a wound site where a negative pressure can be established. The backing layer 220 is preferably sealed to the wound contact layer 222 in a border region around the circumference of the dressing, ensuring that no air is drawn in through the border area, for example via adhesive or welding techniques. The backing layer 220 protects the wound from external bacterial contamination (bacterial barrier) and allows liquid from wound exudates to be transferred through the layer and evaporated from the film outer surface. The backing layer 220 preferably comprises two layers; a polyurethane film and an adhesive pattern spread onto the film. The polyurethane film is preferably moisture vapor permeable and may be manufactured from a material that has an increased water transmission rate when wet. In some embodiments the moisture vapor permeability of the backing layer increases when the backing layer becomes wet. The moisture vapor permeability of the wet backing layer may be up to about ten times more than the moisture vapor permeability of the dry backing layer.

The absorbent layer 221 may be of a greater area than the transmission layer 226, such that the absorbent layer overlaps the edges of the transmission layer 226, thereby ensuring that the transmission layer does not contact the backing layer 220. This provides an outer channel of the absorbent layer 221 that is in direct contact with the wound contact layer 222, which aids more rapid absorption of exudates to the absorbent layer. Furthermore, this outer channel ensures that no liquid is able to pool around the circumference of the wound cavity, which may otherwise seep through the seal around the perimeter of the dressing leading to the formation of leaks. As illustrated in FIGS. 2A-2B, the absorbent layer 221 may define a smaller perimeter than that of the backing layer 220, such that a boundary or border region is defined between the edge of the absorbent layer 221 and the edge of the backing layer 220.

As shown in FIG. 2B, one embodiment of the wound dressing 100 comprises an aperture 228 in the absorbent layer 221 situated underneath the fluidic connector 110. In use, for example when negative pressure is applied to the dressing 100, a wound facing portion of the fluidic connector may thus come into contact with the transmission layer 226, which can thus aid in transmitting negative pressure to the wound site even when the absorbent layer 221 is filled with wound fluids. Some embodiments may have the backing layer 220 be at least partly adhered to the transmission layer 226. In some embodiments, the aperture 228 is at least 1-2 mm larger than the diameter of the wound facing portion of the fluidic connector 11, or the orifice 227.

In particular for embodiments with a single fluidic connector 110 and through hole, it may be preferable for the fluidic connector 110 and through hole to be located in an off-center position as illustrated in FIG. 2A. Such a location may permit the dressing 100 to be positioned onto a patient such that the fluidic connector 110 is raised in relation to the remainder of the dressing 100. So positioned, the fluidic connector 110 and the filter 214 may be less likely to come into contact with wound fluids that could prematurely occlude the filter 214 so as to impair the transmission of negative pressure to the wound site.

Turning now to the fluidic connector 110, preferred embodiments comprise a sealing surface 216, a bridge 211 (corresponding to bridge 120 in FIGS. 1A-1B) with a proximal end 130 and a distal end 140, and a filter 214. The sealing surface 216 preferably forms the applicator previously described that is sealed to the top surface of the wound dressing. In some embodiments a bottom layer of the fluidic connector 110 may comprise the sealing surface 216, such as layer 540 in FIG. 5C below. The fluidic connector 110 may further comprise an upper surface vertically spaced from the sealing surface 216, which in some embodiments is defined by a separate upper layer of the fluidic connector such as layer 510 in FIG. 5C below. In other embodiments the upper surface and the lower surface may be formed from the same piece of material. In some embodiments the sealing surface 216 may comprise at least one aperture 229 therein to communicate with the wound dressing. In some embodiments the filter 214 may be positioned across the opening 229 in the sealing surface, and may span the entire opening 229. The sealing surface 216 may be configured for sealing the fluidic connector to the cover layer of the wound dressing, and may comprise an adhesive or weld. In some embodiments, the sealing surface 216 may be placed over an orifice in the cover layer with optional spacer elements 215 configured to create a gap between the filter 214 and the transmission layer 226. In other embodiments, the sealing surface 216 may be positioned over an orifice in the cover layer and an aperture in the absorbent layer 221, permitting the fluidic connector 110 to provide air flow through the transmission layer 226. In some embodiments, the bridge 211 may comprise a first fluid passage 212 in communication with a source of negative pressure, the first fluid passage 212 comprising a porous material, such as a 3D knitted material, which may be the same or different than the porous layer 226 described previously. The bridge 211 is preferably encapsulated by at least one flexible film layer 208, 210 having a proximal and distal end and configured to surround the first fluid passage 212, the distal end of the flexible film being connected the sealing surface 216. The filter 214 is configured to substantially prevent wound exudate from entering the bridge, and spacer elements 215 are configured to prevent the fluidic connector from contacting the transmission layer 226. These elements will be described in greater detail below.

Preferably, the fluid passage 212 is constructed from a compliant material that is flexible and that also permits fluid to pass through it if the spacer is kinked or folded over.

Suitable materials for the fluid passage 212 include without limitation foams, including open-cell foams such as polyethylene or polyurethane foam, meshes, 3D knitted fabrics, non-woven materials, and fluid channels. In some embodiments, the fluid passage 212 may be constructed from materials similar to those described above in relation to the transmission layer 226. Advantageously, such materials used in the fluid passage 212 not only permit greater patient comfort, but may also provide greater kink resistance, such that the fluid passage 212 is still able to transfer fluid from the wound toward the source of negative pressure while being kinked or bent.

In some embodiments, the fluid passage 212 may be comprised of a wicking fabric, for example a knitted or woven spacer fabric (such as a knitted polyester 3D fabric, Baltex 7970®, or Gehring 879®) or a nonwoven fabric. These materials selected are preferably suited to channeling wound exudate away from the wound and for transmitting negative pressure and/or vented air to the wound site, and may also confer a degree of kinking or occlusion resistance to the fluid passage 212. In some embodiments, the wicking fabric may have a three-dimensional structure, which in some cases may aid in wicking fluid or transmitting negative pressure. In certain embodiments, including wicking fabrics, these materials remain open and capable of communicating negative pressure to a wound area under the typical pressures used in negative pressure therapy, for example between 40 to 150 mmHg. In some embodiments, the wicking fabric may comprise several layers of material stacked or layered over each other, which may in some cases be useful in preventing the fluid passage 212 from collapsing under the application of negative pressure. In other embodiments, the wicking fabric used in the fluid passage 212 may be between 1.5 mm and 6 mm; more preferably, the wicking fabric may be between 3 mm and 6 mm thick, and may be comprised of either one or several individual layers of wicking fabric. In other embodiments, the fluid passage 212 may be between 1.2-3 mm thick, and preferably thicker than 1.5 mm Some embodiments, for example a suction adapter used with a dressing which retains liquid such as wound exudate, may employ hydrophobic layers in the fluid passage 212, and only gases may travel through the fluid passage 212. Additionally, and as described previously, the materials used in the system are preferably conformable and soft, which may help to avoid pressure ulcers and other complications which may result from a wound treatment system being pressed against the skin of a patient.

Preferably, the filter element 214 is impermeable to liquids, but permeable to gases, and is provided to act as a liquid bather and to ensure that no liquids are able to escape from the wound dressing 100. The filter element 214 may also function as a bacterial barrier. Typically the pore size is 0.2 μm. Suitable materials for the filter material of the filter element 214 include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port and/or the cover film over the orifice. For example, the filter element 214 may be molded into the fluidic connector 110, or may be adhered to one or both of the top of the cover layer and bottom of the suction adapter 110 using an adhesive such as, but not limited to, a UV cured adhesive.

It will be understood that other types of material could be used for the filter element 214. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. In some embodiments of the invention, filter element 214 comprises a support layer and an acrylic co-polymer membrane formed on the support layer. Preferably the wound dressing 100 according to certain embodiments of the present invention uses microporous hydrophobic membranes (MHMs). Numerous polymers may be employed to form MHMs. For example, the MHMs may be formed from one or more of PTFE, polypropylene, PVDF and acrylic copolymer. All of these optional polymers can be treated in order to obtain specific surface characteristics that can be both hydrophobic and oleophobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter element 214 may also include an odor absorbent material, for example activated charcoal, carbon fiber cloth or Vitec Carbotec-RT Q2003073 foam, or the like. For example, an odor absorbent material may form a layer of the filter element 214 or may be sandwiched between microporous hydrophobic membranes within the filter element. The filter element 214 thus enables gas to be exhausted through the orifice. Liquid, particulates and pathogens however are contained in the dressing.

The wound dressing 100 may comprise spacer elements 215 in conjunction with the fluidic connector 110 and the filter 214. With the addition of such spacer elements 215 the fluidic connector 110 and filter 214 may be supported out of direct contact with the absorbent layer 220 and/or the transmission layer 226. The absorbent layer 220 may also act as an additional spacer element to keep the filter 214 from contacting the transmission layer 226. Accordingly, with such a configuration contact of the filter 214 with the transmission layer 226 and wound fluids during use may thus be minimized.

In particular for embodiments with a single fluidic connector 110 and through hole, it may be preferable for the fluidic connector 110 and through hole to be located in an off-center position as illustrated in FIGS. 2A-B. Such a location may permit the dressing 100 to be positioned onto a patient such that the fluidic connector 110 is raised in relation to the remainder of the dressing 100. So positioned, the fluidic connector 110 and the filter 214 may be less likely to come into contact with wound fluids that could prematurely occlude the filter 214 so as to impair the transmission of negative pressure to the wound site.

Figure 3A:
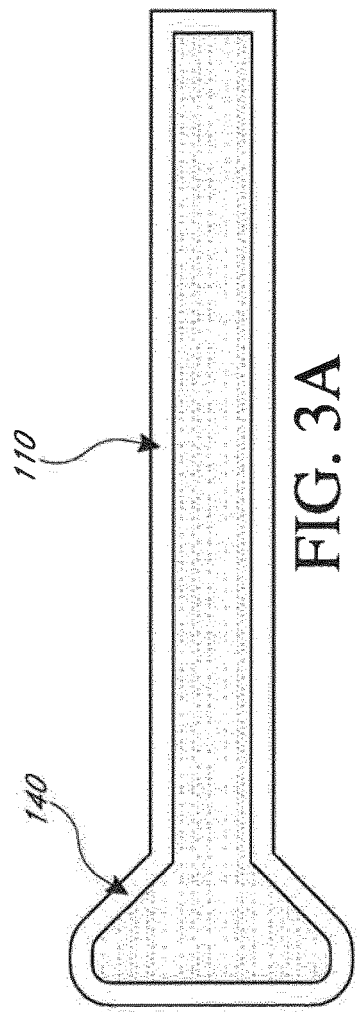
FIGS. 3A-C illustrate various embodiments of the enlarged end of a flexible fluidic connector.
Figure 3B:
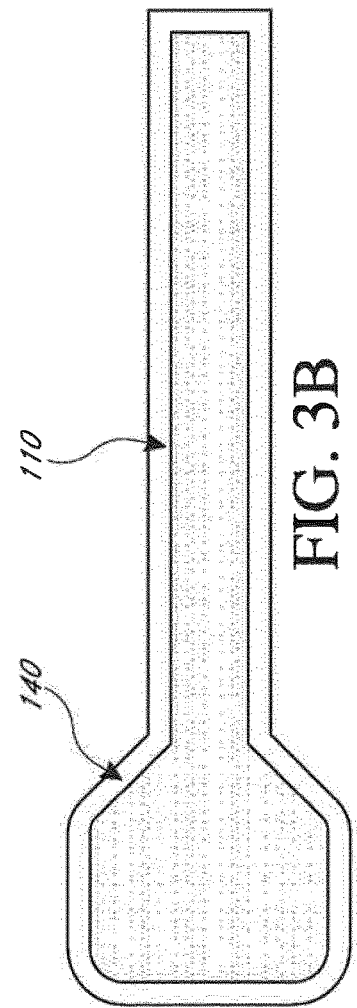
Figure 3C:
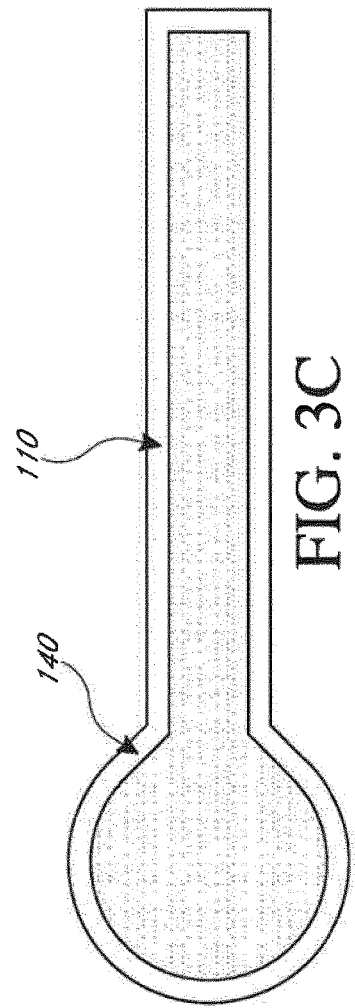

FIGS. 3A-C illustrate various embodiments of the head 140 of the fluidic connector 110. Preferably, the fluidic connector 110 illustrated in FIG. 2A is enlarged at the distal end to be placed over an orifice in the cover layer and the aperture in the absorbent layer of a wound dressing, for example wound dressing 100 of FIGS. 2A-B, and may form a "teardrop" or other enlarged shape. FIG. 3A illustrates a fluidic connector 110 with a substantially triangular head 140. FIG. 3B illustrates a fluidic connector 110 with a substantially pentagonal head 140. FIG. 3A illustrates a fluidic connector 110 with a substantially circular head 140.

Figure 4A:
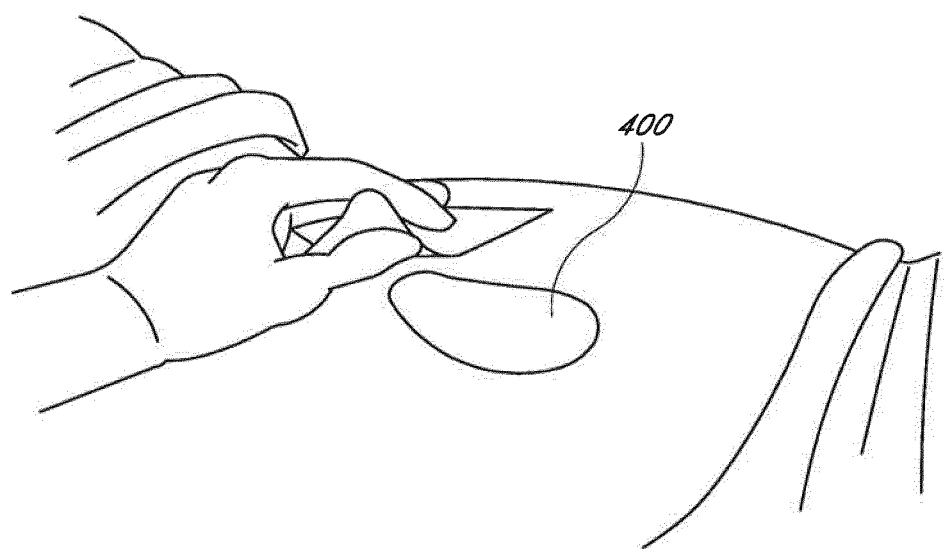
FIGS. 4A-D illustrate the use and application of an embodiment of a wound treatment system onto a patient.

FIGS. 4A-D illustrate the use of an embodiment of a negative pressure therapy wound treatment system being used to treat a wound site on a patient. FIG. 4A shows a wound site 400 being cleaned and prepared for treatment. Here, the healthy skin surrounding the wound site 400 is preferably cleaned and excess hair removed or shaved. The wound site 400 may also be irrigated with sterile saline solution if necessary. Optionally, a skin protectant may be applied to the skin surrounding the wound site 400. If necessary, a wound packing material, such as foam or gauze, may be placed in the wound site 400. This may be preferable if the wound site 400 is a deeper wound.

Figure 4B:
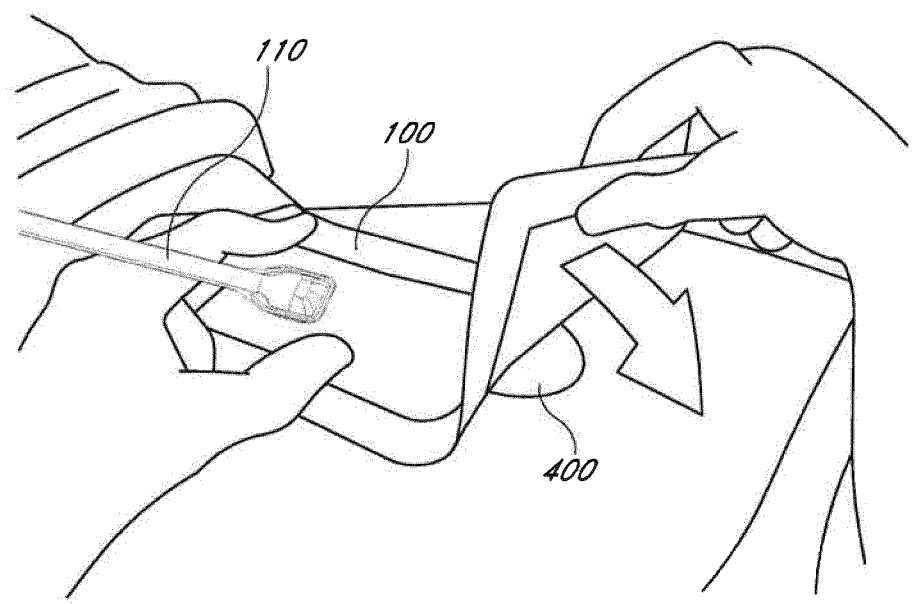

After the skin surrounding the wound site 400 is dry, and with reference now to FIG. 4B, the wound dressing 100 may be positioned and placed over the wound site 400. Preferably, the wound dressing 100 is placed with the wound contact layer over and/or in contact with the wound site 400. In some embodiments, an adhesive layer is provided on the lower surface of the wound contact layer, which may in some cases be protected by an optional release layer to be removed prior to placement of the wound dressing 100 over the wound site 400. Preferably, the dressing 100 is positioned such that the fluidic connector 110 is in a raised position with respect to the remainder of the dressing 10 so as to avoid fluid pooling around the port. In some embodiments, the dressing 100 is positioned so that the fluidic connector 110 is not directly overlying the wound, and is level with or at a higher point than the wound. To help ensure adequate sealing for TNP, the edges of the dressing 100 are preferably smoothed over to avoid creases or folds.

Figure 4C:
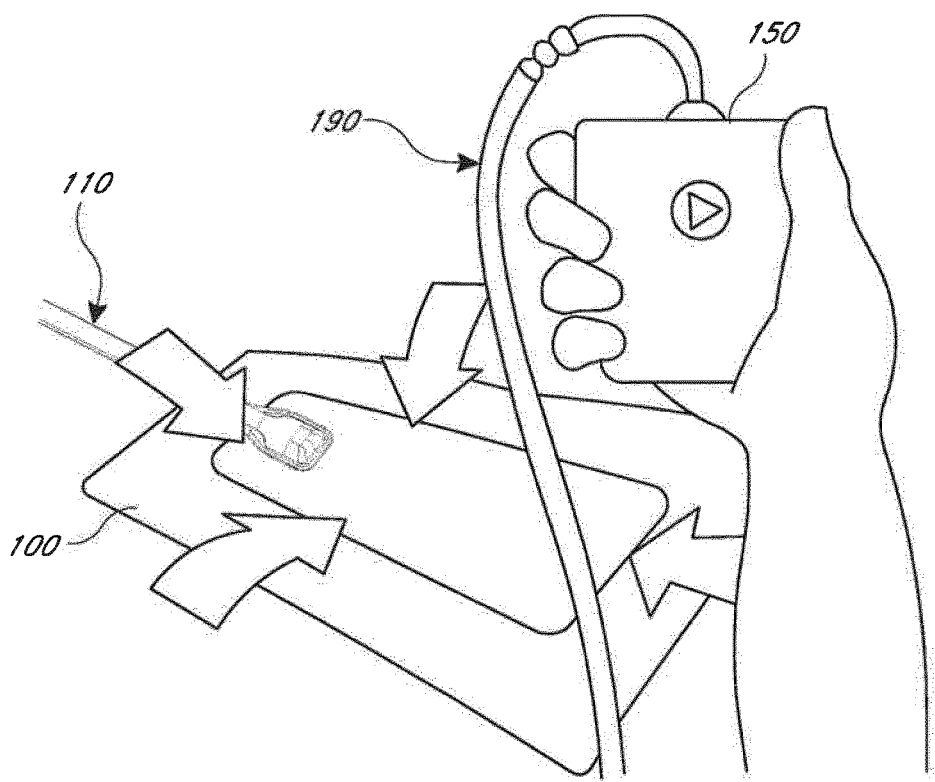

With reference now to FIG. 4C, the dressing 10 is connected to the pump 150. The pump 150 is configured to apply negative pressure to the wound site via the dressing 100, and typically through a conduit. In some embodiments, and as described herein, a fluidic connector 110 may be used to join the conduit 190 from the pump to the dressing 100. Where the fluidic connector is adhered to the top layer of the wound dressing, a length of tubing may be coupled at a first end of the fluidic connector such that the tubing, or conduit, extends away from the fluidic connector parallel to the top of the dressing. In some embodiments the conduit may comprise a fluidic connector. It is expressly contemplated that a conduit may be a soft bridge, a hard tube, or any other apparatus which may serve to transport fluid. Upon the application of negative pressure with the pump 150, the dressing 100 may in some embodiments partially collapse and present a wrinkled appearance as a result of the evacuation of some or all of the air underneath the dressing 100. In some embodiments, the pump 150 may be configured to detect if any leaks are present in the dressing 100, such as at the interface between the dressing 100 and the skin surrounding the wound site 400. Should a leak be found, such leak is preferably remedied prior to continuing treatment.

Figure 4D:
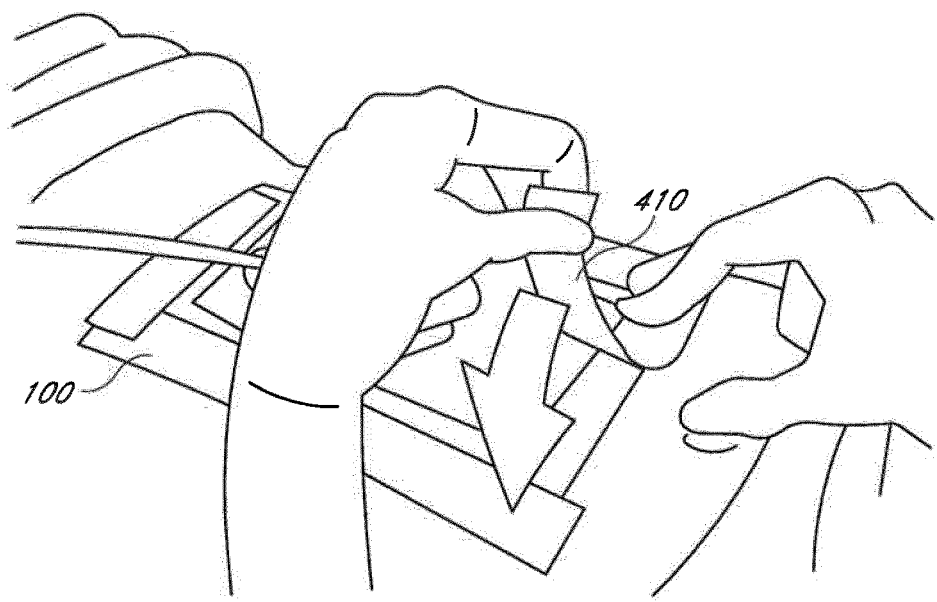

Turning to FIG. 4D, additional fixation strips 410 may also be attached around the edges of the dressing 100. Such fixation strips 410 may be advantageous in some situations so as to provide additional sealing against the skin of the patient surrounding the wound site 400. For example, the fixation strips 410 may provide additional sealing for when a patient is more mobile. In some cases, the fixation strips 410 may be used prior to activation of the pump 150, particularly if the dressing 100 is placed over a difficult to reach or contoured area.

Treatment of the wound site 400 preferably continues until the wound has reached a desired level of healing. In some embodiments, it may be desirable to replace the dressing 100 after a certain time period has elapsed, or if the dressing is full of wound fluids. During such changes, the pump 150 may be kept, with just the dressing 100 being changed.

Further details of dressings and other apparatuses that may be used with the, fluidic connectors described herein include, but are not limited to, dressings described in International Patent Publication WO 2012020440 and WO2014020443, the entireties of which are hereby incorporated by reference.

Figure 5A:
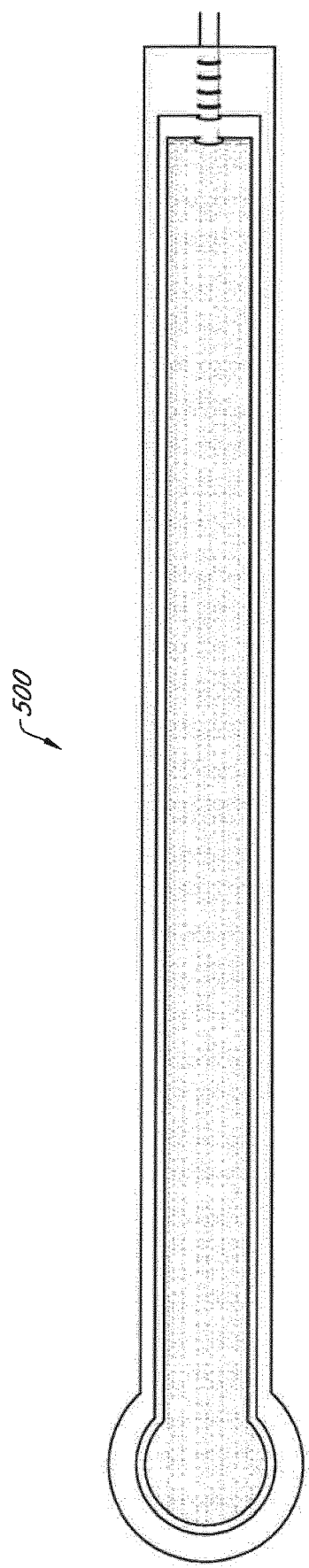
FIG. 5A illustrates a top view of an embodiment of a flexible fluidic connector.
Figure 5B:
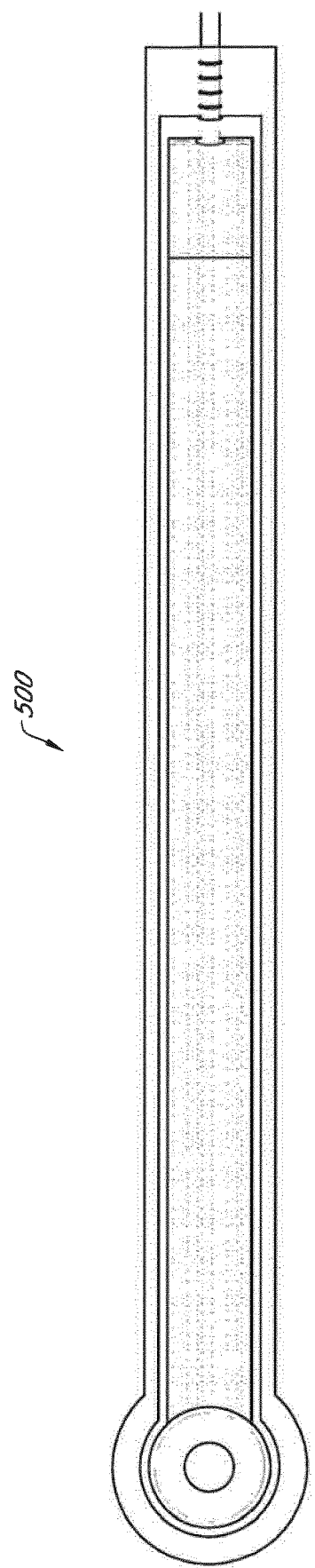
FIG. 5B illustrates a bottom view of an embodiment of a flexible fluidic connector.
Figure 5C:
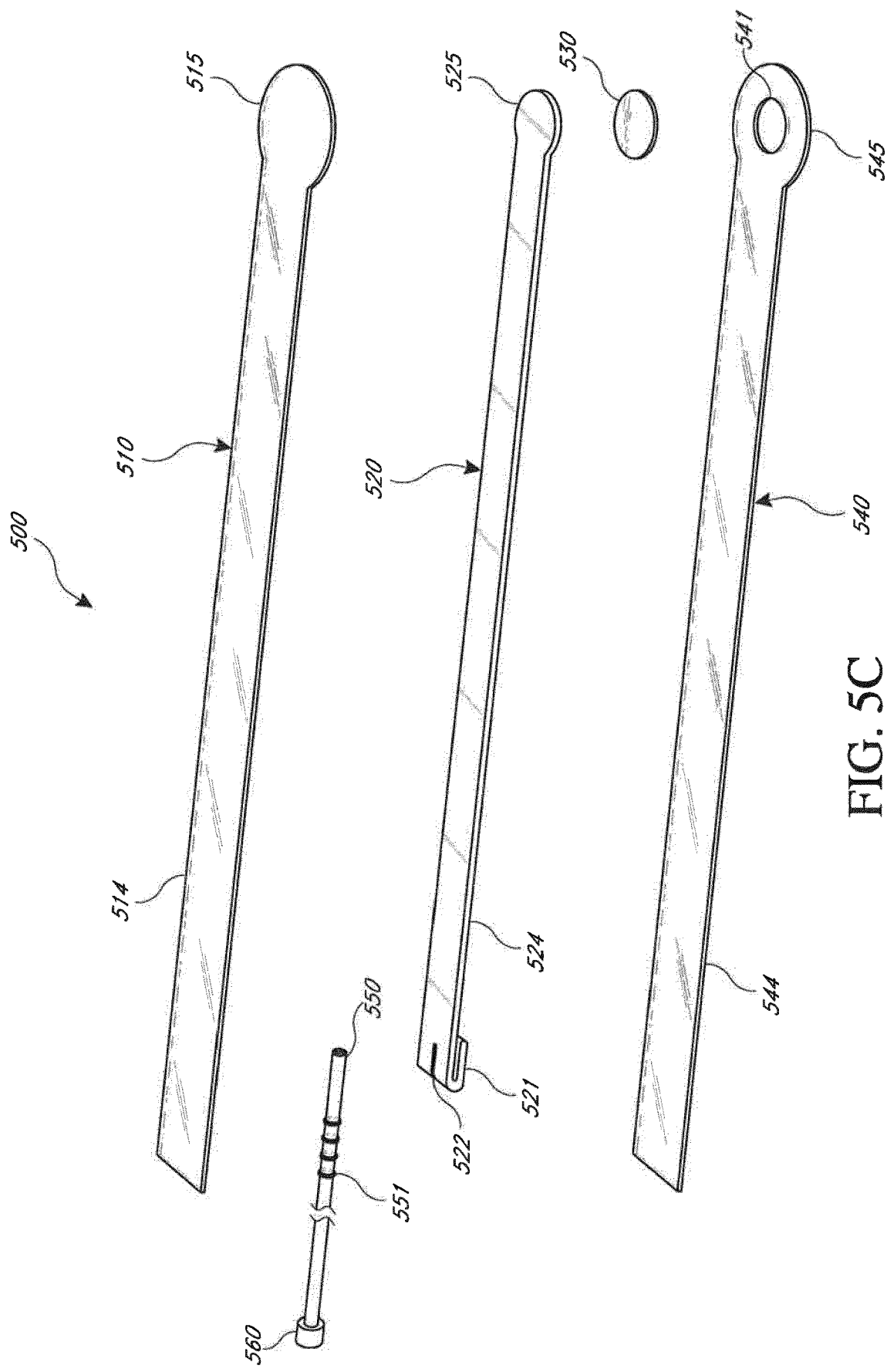
FIG. 5C illustrates a perspective exploded view of an embodiment of a flexible fluidic connector.

FIGS. 5A-B illustrate an embodiment of a flexible port or fluidic connector 500. FIG. 5C illustrates a perspective exploded view the fluidic connector 500 that may be used to connect a wound dressing to a source of negative pressure. The fluidic connector 500 comprises a top layer 510, a spacer layer 520, a filter element 530, a bottom layer 540, and a conduit 550. The conduit optionally comprises a coupling 560. In some embodiments the conduit may comprise a fluidic connector. It is expressly contemplated that a conduit may be a soft bridge, a hard tube, or any other apparatus which may serve to transport fluid. The distal end of the fluidic connector 500 (the end connectable to a dressing) is depicted as having an enlarged circular shape, although it will be appreciated that any suitable shape may be used and that the distal end need not be enlarged. For example, the distal end can have any of the shapes shown in FIGS. 3A-3C above.

The bottom layer 540 may comprise an elongate bridge portion 544, an enlarged (e.g., rounded or circular) sealing portion 545, and an orifice 541. In some embodiments a plurality of orifices may be provided in the bottom layer. Some embodiments of the rounded sealing portion 545 may comprise a layer of adhesive, for example a pressure sensitive adhesive, on the lower surface for use in sealing the fluidic connector 500 to a dressing. For example, the fluidic connector may be sealed to a cover layer of the dressing. The orifice 541 in the bottom layer 540 of the port 500 may be aligned with an orifice in the cover layer of the dressing in order to transmit negative pressure through the dressing and into a wound site.

The top layer 515 may be substantially the same shape as the bottom layer in that it comprises an elongate bridge 514 and an enlarged (e.g., rounded or circular) portion 545. The top layer 515 and the bottom layer 545 may be sealed together, for example by heat welding. In some embodiments, the bottom layer 545 may be substantially flat and the top layer 515 may be slightly larger than the bottom layer 545 in order to accommodate the height of the spacer layer 520 and seal to the bottom layer 545. In other embodiments, the top layer 515 and bottom layer 3145 may be substantially the same size, and the layers may be sealed together approximately at the middle of the height of the spacer layer 520. In some embodiments, the elongate bridge portions 544, 514 may have a length of 10 cm (or about 10 cm) or more, more preferably a length of 20 cm (or about 20 cm) or more and in some embodiments, may be about 69 cm (or 27 cm) long. Some embodiments of the entire fluidic connector, from a proximal-most edge of the top and bottom layers to a distal-most edge of the top and bottom layers, may be between 20 cm and 80 cm (or about 20 cm to about 80 cm) long, more preferably about 60 cm and 80 cm (or between about 60 cm and about 80 cm) long, for example about 70 cm long. In some embodiments, the elongate bridge portions may have a width of between 1 cm and 4 cm (or between about 1 cm and about 4 cm), and in one embodiment, is about 2.5 cm wide. The ratio of the length of the elongate bridge portions 544, 514 to their widths may in some embodiments exceed 6:1, and may more preferably exceed 8:1 or even 10:1. The diameter of the circular portion 545, 515 may be about 3.5 cm in some embodiments.

The bottom and top layers may comprise at least one layer of a flexible film, and in some embodiments may be transparent. Some embodiments of the bottom layer 540 and top layer 515 may be polyurethane, and may be liquid impermeable.

The fluidic connector 500 may comprise a spacer layer 520, such as the 3D fabric discussed above, positioned between the lower layer 540 and the top layer 510. The spacer layer 520 may be made of any suitable material, for example material resistant to collapsing in at least one direction, thereby enabling effective transmission of negative pressure therethrough. Instead of or in addition to the 3D fabric discussed above, some embodiments of the spacer layer 520 may comprise a fabric configured for lateral wicking of fluid, which may comprise viscose, polyester, polypropylene, cellulose, or a combination of some or all of these, and the material may be needle-punched. Some embodiments of the spacer layer 520 may comprise polyethylene in the range of 40-160 grams per square meter (gsm) (or about 40 to about 160 gsm), for example 80 (or about 80) gsm. Such materials may be constructed so as to resist compression under the levels of negative pressure commonly applied during negative pressure therapy.

The spacer layer 520 may comprise an elongate bridge portion 524, an enlarged (e.g., rounded or circular) portion 525, and may optionally include a fold 521. In some embodiments, the elongate bridge portion may have dimensions in the same ranges as the bridge portions of the upper and lower layers described above though slightly smaller, and in one embodiment is about 25.5 cm long and 1.5 cm wide. Similarly, the diameter of the circular portion 525 may be slightly smaller than the diameters of the enlarged ends 545, 515, and in one embodiment is about 2 cm. Some embodiments of the spacer layer 520 may have adhesive on one or both of its proximal and distal ends (e.g., one or more dabs of adhesive) in order to secure the spacer layer 520 to the top layer 510 and/or the bottom layer 540. Adhesive may also be provided along a portion or the entire length of the spacer layer. In other embodiments, the spacer layer 520 may be freely movable within the sealed chamber of the top and bottom layers.

The fold 521 of the spacer layer may make the end of the fluidic connector 500 softer and therefore more comfortable for a patient, and may also help prevent the conduit 550 from blockage. The fold 521 may further protect the end of the conduit 550 from being occluded by the top or bottom layers. The fold 521 may, in some embodiments, be between 1 cm and 3 cm (or between about 1 cm and about 3 cm) long, and in one embodiment is 2 cm (or about 2 cm) long. The spacer layer may be folded underneath itself that is toward the bottom layer 540, and in other embodiments may be folded upward toward the top layer 510. Other embodiments of the spacer layer 520 may contain no fold. A slot or channel 522 may extend perpendicularly away from the proximal end of the fold 521, and the conduit 550 may rest in the slot or channel 522. In some embodiments the slot 522 may extend through one layer of the fold, and in others it may extend through both layers of the fold. The slot 522 may, in some embodiments, be 1 cm (or about 1 cm) long. Some embodiments may instead employ a circular or elliptical hole in the fold 521. The hole may face proximally so that the conduit 550 may be inserted into the hole and rest between the folded layers of spacer fabric. In some embodiments, the conduit 550 may be adhered to the material of the fold 521, while in other embodiments it may not.

The fluidic connector 500 may have a filter element 530 located adjacent the orifice 541, and as illustrated is located between the lower layer 540 and the spacer layer 520. The filter element 530 may be positioned across the opening or orifice of the fluidic connector 500. The filter element 530 is impermeable to liquids, but permeable to gases. The filter element may be similar to the element described above with respect to FIG. 1B, and as illustrated may have a round or disc shape. The filter element 530 can act as a liquid bather, to substantially prevent or inhibit liquids from escaping from the wound dressing, as well as an odor bather. The filter element 530 may also function as a bacterial bather. In some embodiments, the pore size of the filter element 530 can be approximately 0.2 µm. Suitable materials for the filter material of the filter element include 0.2 micron Gore™ expanded PTFE from the MMT range, PALL Versapore™ 200R, and Donaldson™ TX6628. The filter element 530 thus enables gas to be exhausted through the orifice. Liquid, particulates and pathogens however are contained in the dressing. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. In some embodiments, the filter element 530 may be adhered to one or both of top surface of the bottom layer 540 and the bottom surface of the spacer layer 520 using an adhesive such as, but not limited to, a UV cured adhesive. In other embodiments, the filter 530 may be welded to the inside of the spacer layer 520 and to the top surface of the bottom layer 540. The filter may also be provided adjacent the orifice on a lower surface of the bottom layer 540. Other possible details regarding the filter are disclosed in U.S. Patent Pub. No. 2011/0282309 and incorporated by reference herein.

The proximal end of the fluidic connector 500 may be connected to the distal end of a conduit 550. The conduit 550 may comprise one or more circular ribs 551. The ribs 551 may be formed in the conduit 550 by grooves in a mold during the manufacturing of the conduit. During heat welding of the upper and lower layers 515, 545 melted material from those layers may flow around the ribs 551, advantageously providing a stronger connection between the conduit 550 and the layers. As a result, it may be more difficult to dislodge the conduit 550 out from between the layers during use of the fluidic connector 500.

The proximal end of the conduit 550 may be optionally attached to a coupling 560. The coupling 560 may be used to connect the fluidic connector 500 to a source of negative pressure, or in some embodiments to an extension conduit which may in turn be connected to a source of negative pressure. As explained in more detail below with respect to FIGS. 8A and 8B, the proximal end of the conduit 550, which is inserted into the spacer fabric 520, may be shaped in such a way to reduce the possibility of occlusion. For example, some embodiments may have a triangular portion cut out of the end of the conduit, and other embodiments may have a plurality of holes therethrough.

Figure 6:
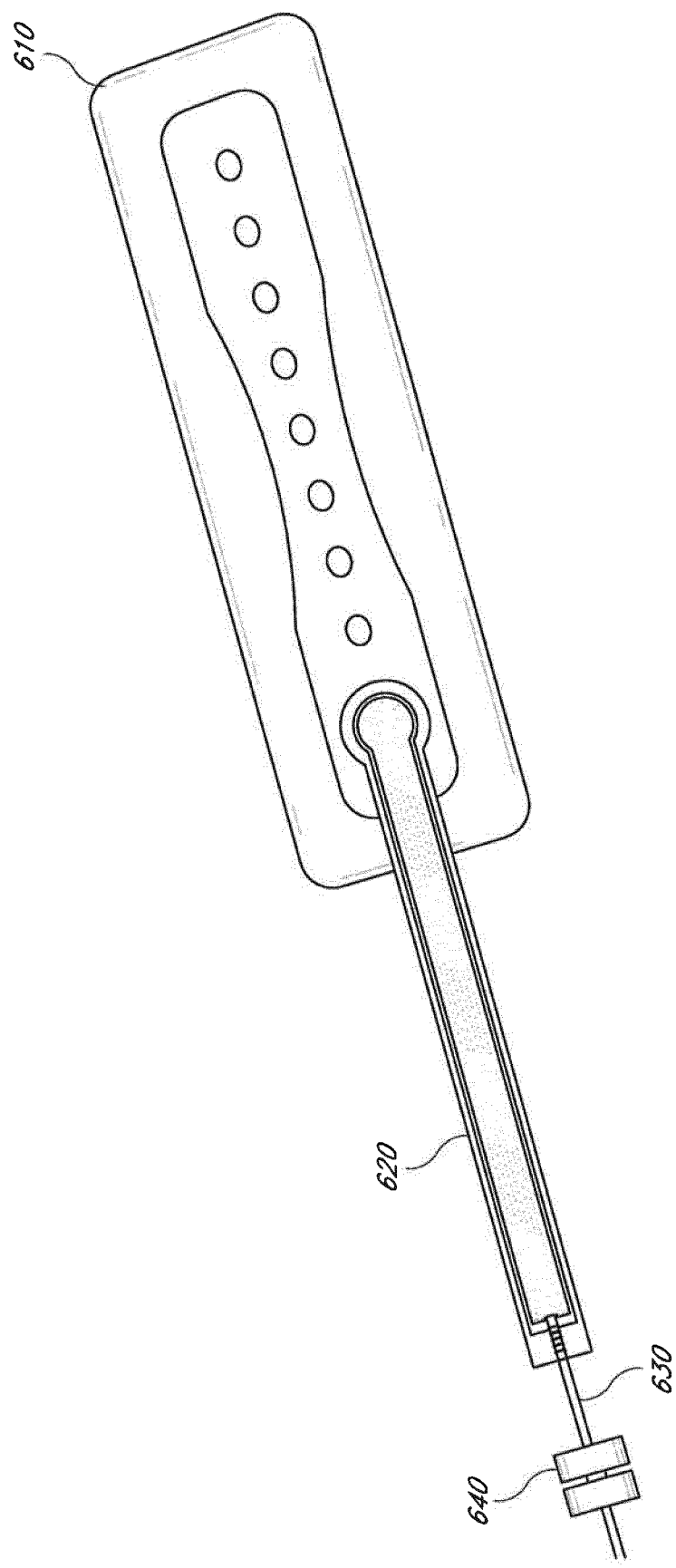
FIG. 6 illustrates an embodiment of a flexible fluidic connector attached to a wound dressing.

FIG. 6 illustrates an embodiment of a wound dressing 610 with a fluidic connector 620 such as described above with respect to FIGS. 5A-C attached to the dressing. The fluidic connector 620 may be the fluidic connector described above in FIGS. 5A-C. The fluidic connector 620 may comprise a conduit 630 and a coupling 640 for connecting the fluidic connector to a source of negative pressure or to an extension conduit. Although in this depiction the fluidic connector 620 is connected over a circular window in the obscuring layer of the dressing 610, in other embodiments the fluidic connector 620 may be connected over a maltese cross in the obscuring layer. In some embodiments, the maltese cross may be of a larger diameter than the fluidic connector 620 and may be at least partially viewable after the fluidic connector 620 is attached to the dressing 610. Further details regarding the dressing 610 and other dressings to which the fluidic connector can be connected are described in International Patent Publications WO2012020440 and WO2014020443, the entireties of which are hereby incorporated by reference. Further details regarding wound dressings and fluidic connectors can be found in U.S. patent application Ser. No. 14/715,527, titled "FLUIDIC CONNECTOR FOR NEGATIVE PRESSURE WOUND THERAPY" filed May 18, 2015, published as US 2016/0339158, the entirety of which are hereby incorporated by reference.

A negative pressure wound therapy system may include a three-dimensional filter element to prevent or inhibit wound fluid or exudate from escaping from a wound dressing. In some embodiments, the three-dimensional filter element may be placed within the wound dressing and/or the fluidic connector, and replace the filter element such as the filter element 214 described in relation to FIG. 2B, or the filter element 530 described in relation to FIG. 5C. In some embodiments, a negative pressure wound therapy system may contain both the three-dimensional filter element and the filter element such as the filter element 214 described in relation to FIG. 2B or the filter element 530 described in relation to FIG. 5C.

Figure 7A:
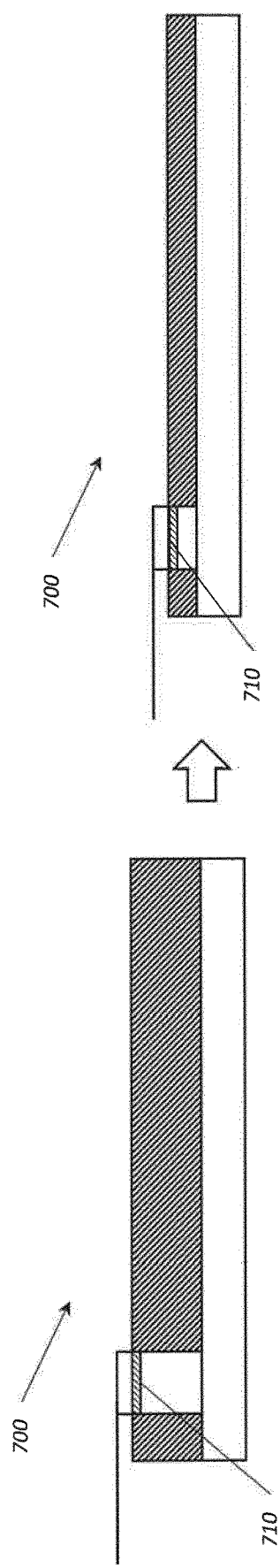
FIGS. 7A-B illustrate an embodiment of a flexible fluidic connector attached to a wound dressing, and another embodiment of a flexible fluidic connector including a three-dimensional filter element attached to a wound dressing.
Figure 7B:
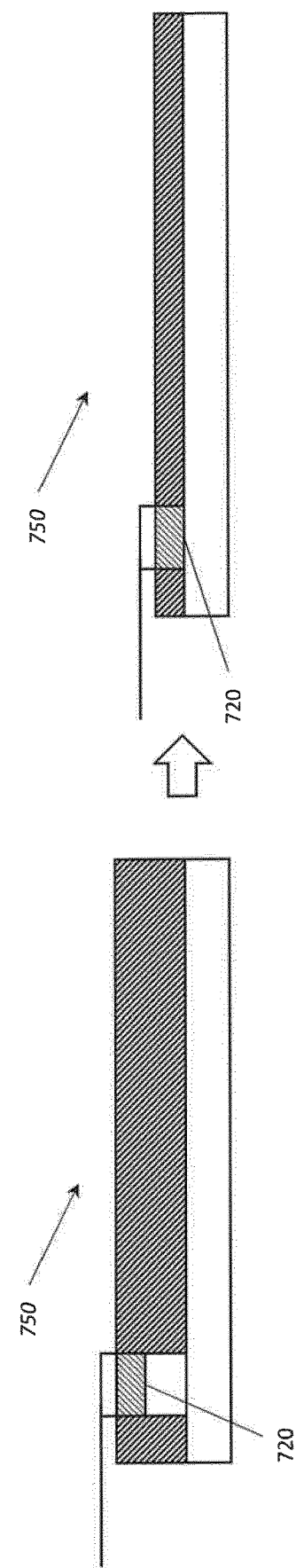

The three-dimensional filter element may have a substantial thickness or height perpendicular to a width, a length, and/or a diameter, and thus define three-dimensional shape, as compared with the filter elements 214 or 530, which are relatively flatter and have minimal thickness or height. Thus, the three-dimensional filter may have more surface area than a two-dimensional filter having a same cross-sectional area. For example, a cylindrical three-dimensional filter element having a cross-sectional radius of r and a height of h may have a surface area of 2 $\pi rh$ (side wall)+$\pi r^2$ (bottom surface), while a circular two-dimensional filter having a radius r will only have a surface area of $\pi r^2$. The increased surface area of the three-dimensional filter may allow improved filtering capacity and better air flow even when the filter is partially blocked. Such advantage of three-dimensional filters is further depicted in FIGS. 7A-B, wherein a NPWT system 700 having a two-dimensional filter 710, and another NPWT system 750 having a three dimensional filter 720 are schematically shown. In FIGS. 7A and 7B, the NPWT systems 700 and 750 without negative pressure applied are shown on the left, while the NPWT systems 700 and 750 under negative pressure are shown on the right. As shown in FIG. 7B, the three-dimensional filter element 720 may be configured to maintain its height under negative pressure, thereby maintain its increased surface area.

Figure 8:
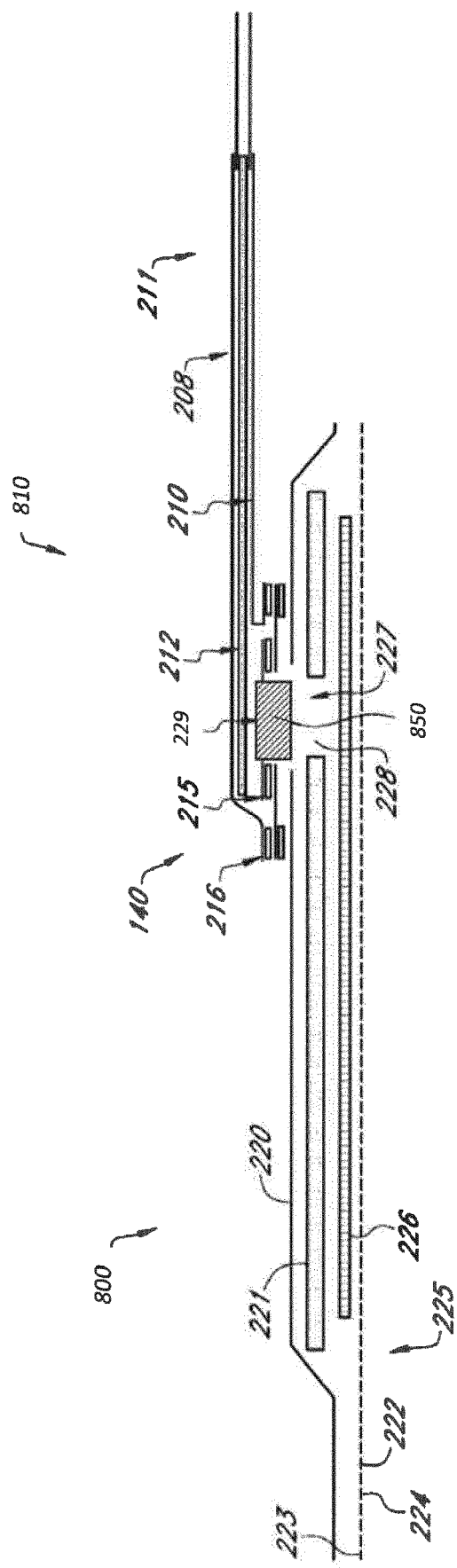
FIG. 8 illustrates a cross-section of an embodiment of a fluidic connector connected to a wound dressing with a three-dimensional filter.

FIG. 8 illustrates a cross-sectional view through an embodiment of a negative pressure wound therapy apparatus having a wound dressing 800 along with a fluidic connector 810. Each of the wound dressing 800 and the fluidic connector 810 may be constructed similar to the wound dressing 100 and the fluidic connecter 110 shown in and described in relation to FIG. 2B or elsewhere in the specification, respectively, except as noted below. Thus, the references numerals used to designate the various components of the wound dressing 800 and the fluidic connector 810 are identical to those used for identifying the corresponding components of the wound dressing 100 and the fluidic connector 110.

In some embodiments, such as shown in FIG. 8, the fluidic connector 810 may include a three-dimensional filter element 850. The three-dimensional filter element 850 may be positioned across the opening 229 in the sealing surface 216 of the fluidic connector 810, and may span the entire opening 229 and/or the aperture 227 of the cover layer 220. In some embodiments, the three-dimensional filter element 850 may located within the fluidic connector. In some embodiments, the filter element 850 may extrude out or extend out of the fluidic connector 810. The extruded-out portion of the filter element 850 may pass and extend through the aperture 227 of the cover layer 220 and/or the aperture or through-hole 228 of the absorbent layer 221 of the dressing 800. In some embodiments, the aperture or through-hole 228 may be a recess which only partially extends through the thickness of the absorbent layer 221. The aperture, through-hole, and the recess 228 of the absorbent layer 221 are interchangeable variations of cut-outs in the absorbent layer 221, and these terms may be used interchangeably hereinafter. In some embodiments, the sealing surface 216 may be placed over the orifice 227 in the cover layer with optional spacer elements 215 configured to offset the height or thickness of the three-dimensional filter element 850, such that only pre-determined portion of the three-dimensional filter 850 extends out of the sealing surface of the fluidic connector through the opening 229 and maintains a gap between the filter element 850 and the transmission layer 226. In some embodiments, the filter element 850 may be entirely within the fluidic connector 810 and does not extend to the wound dressing 800.

Alternatively, a three-dimensional filter may be placed at/on the wound dressing 800. For example, in some embodiments, the three-dimensional filter may be placed within the aperture 227 of the cover layer 220 and the aperture 228 of the absorbent layer 221. In some embodiments, the three-dimensional filter may be thinner than the depth of the aperture 228, such that the three-dimensional filter is fully embedded in the aperture 228. In some embodiments, the three-dimensional filter may be thicker than the depth of the aperture 228, such that the three-dimensional filter element extrudes out from the absorbent layer/wound dressing through the aperture 228. However, the three-dimensional filter element may be placed at any location relative to the absorbent layer 221. In some embodiments, the three-dimensional filter may be placed above the absorbent layer 221, or next to the side wall of the absorbent layer 221.

The three-dimensional filter element may be fixed to the fluidic connector or the wound dressing element by any suitable means, such as glue or an adhesive, as explained below in further detail. In some embodiments, the three-dimensional filter element may be molded with the fluidic connector or the wound dressing as an integrated part.

The filter element 850 may be constructed to conform to the shape and the size of the opening 229 and/or the aperture in the wound dressing 800. In some embodiments, the filter 850 may have the exact same shape and size with the aperture 228 and/or the opening 229, such that wound exudate does not leak along the gap between the perimeter of the three-dimensional filter element 850 and the aperture 228 or the opening 229. In some embodiments, the three-dimensional filter element has length or width greater than 1 mm, 3 mm, 5 mm, 1 cm, 3 cm or 5 cm. Also, the three-dimensional filer 850 may be constructed to have a height or thickness such that the gap between the three-dimensional filter and the bottom of the recess 228 or the transmission layer 226 may be maintained under negative pressure. For example, the height of the three-dimensional filter 850 may not be greater than the thickness of the absorbent layer 221 under negative pressure, such that the three-dimensional filter 850 does not reach the transmission layer 226 through the aperture 228 even when the absorbent layer 221 collapses under negative pressure. However, at the same time, the three-dimensional filter element may have a certain amount of thickness or height to have an advantage of having a three-dimensional structure described in this section or elsewhere in the specification. In some embodiments, the three-dimensional filter 850 may have a thickness greater than, for example, 1 mm, 2 mm, 3 mm, 5 mm, 1 cm or 5 cm. In some embodiments, the three-dimensional filter 850 may have a thickness or height greater than its length or width. In some embodiments, the three-dimensional filter 850 may have a thickness or height smaller than its length or width.

The three-dimensional filter may have any suitable shape. For example, in some embodiments, the filter element 850 may be cylindrical or cuboid. In some embodiments, the cross-section along the horizontal plane of the filter element 850 may have a circular, elliptical, square, rectangular, diamond, or any other suitable cross-sectional shape.

Figure 9:
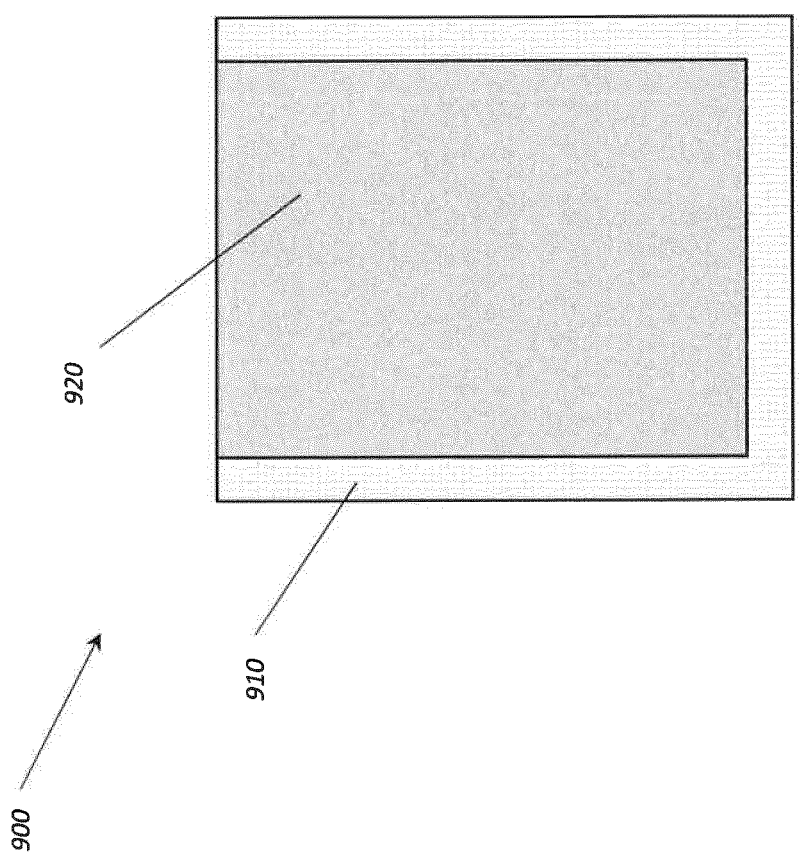
FIG. 9 illustrates a cross-section of an embodiment of a three-dimensional filter.

The three-dimensional filter element may include one or more filter layers constructed from filter materials forming the three-dimensional shape. In some embodiments, the three-dimensional filter element also includes an optional spacer to maintain the three-dimensional shape of the filter element. FIG. 9 illustrates a vertical cross-sectional view of an embodiment of a three-dimensional filter element 900 similar to the three-dimensional filter element 850 described in relation to FIG. 8 or any three-dimensional filter elements described in this section or elsewhere in the specification. The three-dimensional filter element 900 may include a filter layer 910 and a spacer material core 920. In some embodiments, the filter layer 910 may at least partially enclose a spacer material core 920, such that the filter layer is placed on the outside of the three-dimensional filter element to maximize filtering area, while the spacer material core inside allows air flow and supports the overall structure of the three-dimensional filter element. Having the spacer material core may also contribute to the ease of constructing the three-dimensional filter element, as it may be easier to apply the filter layer over the three-dimensional-structured spacer material core than building a three-dimensional structure solely with the filter material.

Preferably, the filter layer 910 is impermeable to liquids, but permeable to gases, and may be constructed from any materials suitable for the filter element 214 described in relation to FIG. 2B or the filter element 530 described in relation to FIG. 5C. For example, the filter layer 910 may be constructed from 0.2 micron Gore™ expanded PTFE from the MMT range, PALL Versapore™ 200R, PALL Versapore™ 1200R and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. In some embodiments, the filter material 910 may be hydrophobic. A portion of the filter layer can be attached or sealed to the fluidic connector and/or the wound dressing. For example, the filter layer 910 may be molded into the fluidic connector, or may be adhered to one or both of the wound dressing and the suction adapter using an adhesive such as, but not limited to, a UV cured adhesive, as described further below in relation to FIGS. 10A-11B. The filter layer 910 of the three-dimensional filter element 900 may be constructed not to collapse substantially under negative pressure, such that it maintains the unobstructed air flow under the negative pressure.

The spacer material core 920 may be constructed from any soft spacer material that allows an air flow throughout. For example, in some embodiments, the spacer material core 920 may be constructed from materials suitable for the absorbent layer 220 described in relation to FIG. 2B, such as ALLEVYN™ foam, Freudenberg 114-224-4 and/or ChemPosite™ 11C-450, Baltex 7970®, or fibrous material such as cellulose. The filter material 910 may be adhered to the spacer material core 910 using an adhesive such as, but not limited to, a UV cured adhesive. The spacer material core 920 may also be constructed from any soft spacer material that allows an air flow throughout. For example, in some embodiments, the spacer material core 920 may be constructed from materials suitable for the spacer layer 520, the spacer element 215, or any other spacers described elsewhere in the specification, such as a knitted polyester 3D fabric, Gehring 879®, a fabric comprising comprise viscose, polyester, polypropylene, cellulose, or a combination of some or all of these.

A negative pressure wound therapy system including the three-dimensional filter element may be constructed in various ways. FIGS. 10A-11B illustrates different embodiments of a wound dressing and a fluidic connector having a three-dimensional filter element.

Figure 10A:
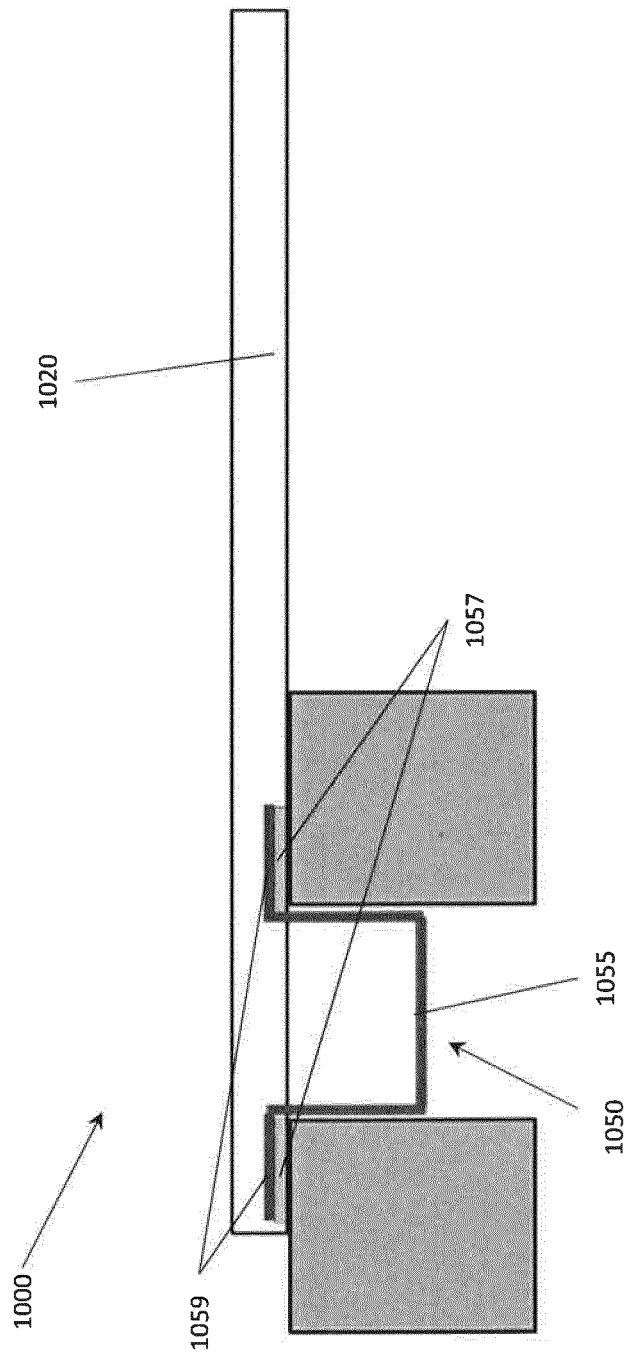
FIG. 10A illustrates a schematic view of an embodiment of a fluidic connector having a three-dimensional filter attached to a wound dressing.

FIG. 10A illustrates a schematic view of an embodiment of the NPWT system 1000 where the three-dimensional filter element 1050 is attached to the fluidic connector 1020. In some embodiments, the filter element 1050 may have a filter layer 1055 with a flap portion 1059, and the flap portion 1059 may adhere to the fluidic connector 1020, for example, using an adhesive 1057.

Figure 10B:
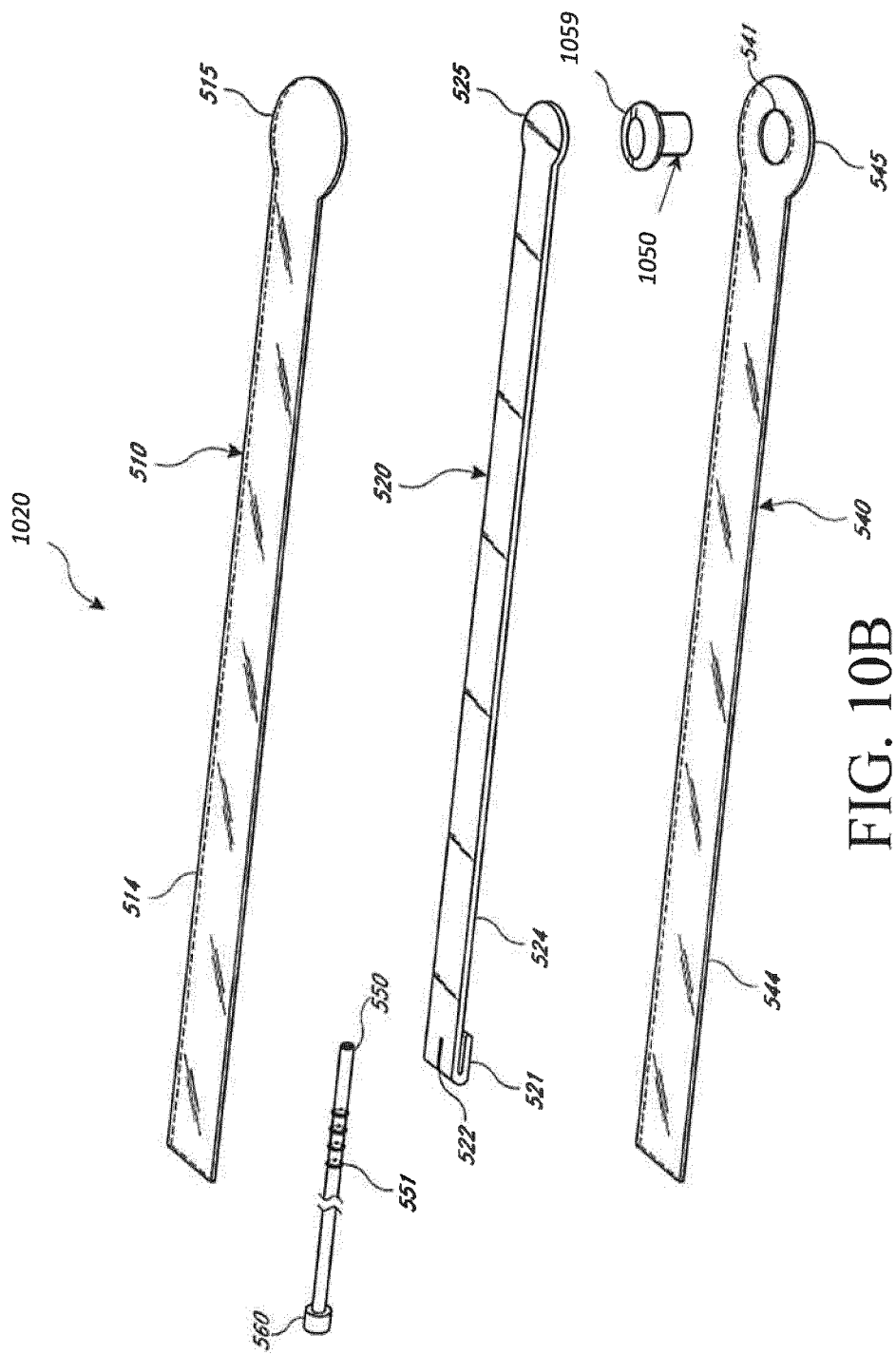
FIG. 10B illustrates a perspective exploded view of the fluidic connector of FIG. 10A.

FIG. 10B illustrates a plan view of an embodiment of the fluidic connector 1020. The fluidic connector 1020 may be constructed similar to the fluidic connector 500 shown in and described in relation to FIG. 5C or elsewhere in the specification, except that the fluidic connector 1020 includes the three-dimensional filter element 1050, instead of the filter element 530. Thus, the references numerals used to designate the various components of the fluidic connector 1020 are identical to those used for identifying the corresponding components of the fluidic connector 500.

As shown in FIG. 10B, in some embodiments, the filter element 1050 may adhere to the fluidic connector 1020 in a similar fashion to the filter element 530 adhering to the fluidic connector 500 as described in relation to FIG. 5C. For example, the filter element 1050 may be located adjacent the orifice of the fluidic connector orifice 541, and the flap portion 1059 may be located between the lower layer 540 and the spacer layer 520. The filter element 1050 may be positioned across the opening or orifice 541 of the fluidic connector 1020. In some embodiments, the flap portion 1059 of the filter element 1050 may be adhered to one or both of the top surface of the bottom layer 540 and the bottom surface of the spacer layer 520 using an adhesive such as, but not limited to, a UV cured adhesive. In other embodiments, the flap portion 1059 or the entire filter element 1050 may be welded to the inside of the spacer layer 520 and to the top surface of the bottom layer 540. The filter element 1050 may also be provided adjacent the orifice on a lower surface of the bottom layer 540.

In some embodiments, the filter element 1050 may not include the flap portion 1057, and the mechanism to attach the filter element 1050 to the fluidic connector 1020 may not be limited to the above embodiment. For example, the filter element may be adhered or welded to any portion of the fluidic connector 1020 using any suitable methods, so as to prevent wound fluid and exudate from the wound dressing leaks into the fluidic connector under negative pressure.

In some embodiments, the filter element 1050 may further include a spacer material core within the space defined by the filter layer 1055 as described above in relation to FIG. 9. To construct such three-dimensional filters, in some embodiments, a filter material for the filter layer 1055 may be cut into a thin strip and looped into a tube. Then, a spacer material may be cut into a disc using, for example, a clicker press, to form the spacer material core. Then, the tube of the filter material may be placed around the disc of the spacer material core and held in place with, for example, an adhesive, to provide an intermediate assembly. Then, a disc of the filter material may be prepared, and the disc of the filter material may be attached to the bottom of the intermediate assembly with, for example, an adhesive, to provide a three-dimensional filter element 1050. Then the filter element may be inserted into aperture of the lower layer of the fluidic connector 1110 and fixed onto the lower layer of the fluidic connector 1110.

In some embodiments, a three-dimensional filter element may be placed within a wound dressing such as the wound dressing 100 described in relation with FIG. 2B. In such embodiments, each an absorbent layer and a top film may be cut to create a hole. Then a spacer layer may be placed on a wound contact layer sheet, followed by placement of the absorbent layer. The three-dimensional filter element may be put in place with the absorbent layer hole, and then the dressing may be covered by the top film sheet, in alignment with the hole of the absorbent layer. Holes of the absorbent layer and the top film sheet may be aligned for the fluidic connector attachment.

Figure 11A:
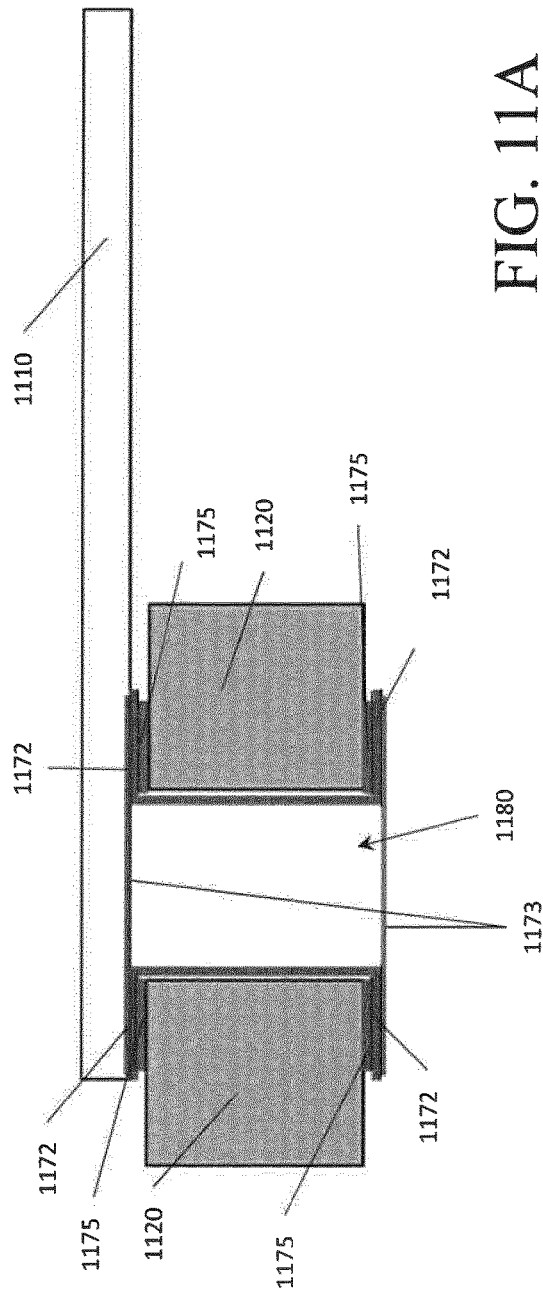
FIG. 11A illustrates a schematic view of an embodiment of a fluidic connector and a wound dressing having a three-dimensional filter.

The three-dimensional filter element may be placed into the wound dressing in various methods. In some embodiments, such as shown in FIG. 11A, a filter material may be cut into a thin strip and looped into a tube, then slits may be cut into the top and bottom of the tube to form foldable flaps 1172. Then the tube may be inserted into the aperture 1180 of absorbent layer 1120 of the wound dressing, and the flaps may be folded and attached onto top and bottom side of the absorbent layer 1120, for example with an adhesive 1175. Then two pieces of the filter material 1173, for example in a square-shaped filter material, may cover each side of the tube. This assembly of the filter material and the absorbent layer can be then placed on top of a spacer layer and under a cover layer to form a wound dressing, and the fluidic connector 1110 may be applied over the wound dressing.

Figure 11B:
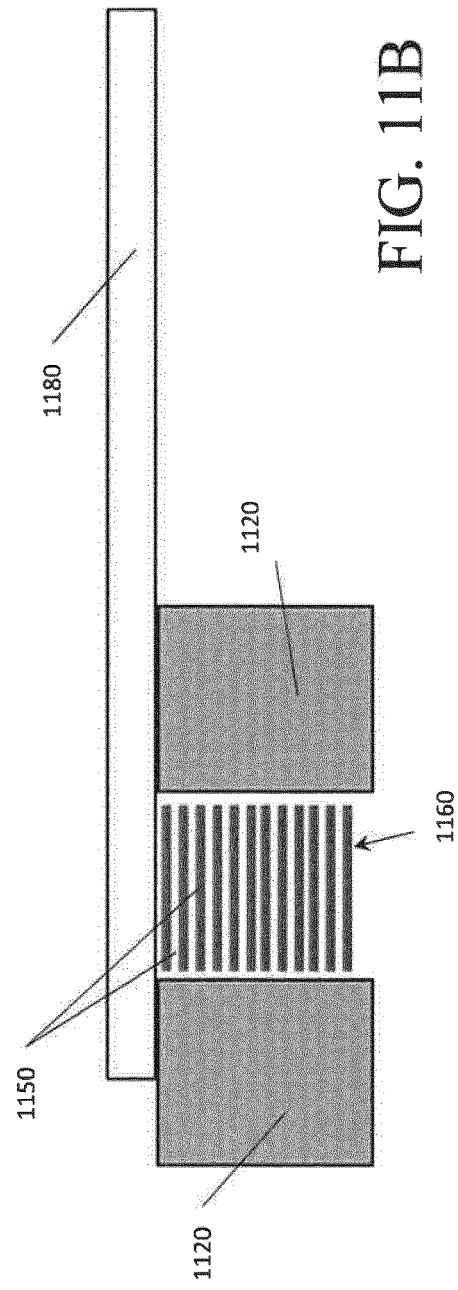
FIG. 11B illustrates a schematic view of an embodiment of a fluidic connector and a wound dressing having a three-dimensional filter.

In some embodiments, such as shown in FIG. 11B, a three-dimensional filter element may be constructed from multiple layers of the filter material. The filter material may be cut into discs 1150, which will be stacked and placed within the aperture 1160 of the absorbent layer 1120. The filter material discs 1150 may not be fixed or attached, as they can be contained within the area after a fluidic connector 1110 is attached to the wound dressing 1100 and cover the aperture 1160.

While FIGS. 10A to 11B and associated descriptions have described locations of the three-dimensional filter within the NPWT system and how the three-dimensional filter can be attached to the wound dressing or the fluidic connector, these embodiments have been presented by way of example only, and locations of the three-dimensional filter within the NPWT system and method to provide and install the three-dimensional filter element are not limited by embodiments of FIGS. 10A-11B or any other embodiments described elsewhere in the specification. The three-dimensional filter element may be placed in any suitable location by any suitable methods so as to prevent the wound exudate from flowing out of the wound dressing. For example, the three-dimensional filter may be placed above the wound dressing or next to the wound dressing.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. A wound treatment apparatus comprising:
   a wound dressing comprising:
      a cover layer comprising an aperture; and
      an absorbent layer comprising a recess extending vertically at least partially through a thickness of the absorbent layer, the absorbent layer positioned beneath the cover layer; and a fluidic connector comprising an orifice, wherein the fluidic connector is configured to provide negative pressure to the wound dressing through the orifice in the fluidic connector and the aperture in the cover layer, wherein the fluidic connector comprises a sealing surface surrounding the orifice configured to seal the fluidic connector to the wound dressing; and a three-dimensional filter element configured to prevent wound exudate from exiting the wound dressing through the aperture of the cover layer when negative pressure is provided to the wound dressing, wherein the three-dimensional filter element is adhered to an interior portion of the fluidic connector and extends from a wound dressing facing surface of the fluidic connector through the orifice of the fluidic connector and through the aperture in the cover layer and extends vertically along at least a portion of the thickness of the absorbent layer within the recess.

2. The wound treatment apparatus of claim 1, wherein the three-dimensional filter element spans the aperture in the cover layer.

3. The wound treatment apparatus of claim 1, wherein the recess is a through-hole which extends through the entire thickness of the absorbent layer.

4. The wound treatment apparatus of claim 1, wherein the three-dimensional filter element is at least partially cylindrically shaped or cuboid-shaped.

5. The wound treatment apparatus of claim 1, wherein the three-dimensional filter element further comprises a filter layer.

6. The wound treatment apparatus of claim 5, wherein the filter layer is oleophobic.

7. The wound treatment apparatus of claim 5, wherein the three-dimensional filter element further comprises a spacer core, wherein the spacer core is at least partially enclosed by the filter layer.

8. A wound treatment apparatus comprising:
a wound dressing comprising:
a cover layer comprising an aperture; and
an absorbent layer positioned beneath the cover layer, the absorbent layer having a thickness;
a fluidic connector comprising an orifice, wherein the fluidic connector is configured to provide negative pressure to the wound dressing through the orifice in the fluidic connector and the aperture in the cover layer, wherein the fluidic connector comprises a sealing surface surrounding the orifice configured to seal the fluidic connector to the wound dressing; and
a three-dimensional filter element configured to prevent wound exudate from exiting the wound dressing through the aperture of the cover layer when negative pressure is provided to the wound dressing, wherein the three-dimensional filter element is adhered to an interior portion of the fluidic connector and extends from a wound dressing facing surface of the fluidic connector through the orifice of the fluidic connector and through the aperture in the cover layer.

9. The wound treatment apparatus of claim 8, wherein the three-dimensional filter element extends along at least a portion of the thickness of the absorbent layer.

10. The wound treatment apparatus of claim 9, wherein the absorbent layer comprises a recess extending vertically at least partially through a thickness of the absorbent layer, and wherein the three-dimensional filter element extends vertically along at least a portion of the thickness of the absorbent layer within the recess.

11. The wound treatment apparatus of claim 8, wherein the three-dimensional filter element is above the absorbent layer.

12. The wound treatment apparatus of claim 8, wherein the three-dimensional filter element spans the aperture in the cover layer.

13. The wound treatment apparatus of claim 8, wherein the three-dimensional filter element is at least partially cylindrically shaped or cuboid-shaped.

14. The wound treatment apparatus of claim 8, wherein the three-dimensional filter element further comprises a filter layer.

15. The wound treatment apparatus of claim 14, wherein the filter layer oleophobic.

16. The wound treatment apparatus of claim 14, wherein the three-dimensional filter element further comprises a spacer core, wherein the spacer core is at least partially enclosed by the filter layer.

17. The wound treatment apparatus of claim 1, wherein the fluidic connector comprises a top layer and a lower layer, wherein the top layer and the lower layer are sealed to form the fluidic connector, wherein the lower layer comprises a first side facing the top layer and an opposite second side.

18. The wound treatment apparatus of claim 17, wherein the three-dimensional filter element comprises a flap portion, wherein the flap portion is configured to be located on the first side of the lower layer.

19. The wound treatment apparatus of claim 8, wherein the fluidic connector comprises a top layer and a lower layer, wherein the top layer and the lower layer are sealed to form the fluidic connector, wherein the lower layer comprises a first side facing the top layer and an opposite second side.

20. The wound treatment apparatus of claim 19, wherein the three-dimensional filter element comprises a flap portion, wherein the flap portion is configured to be located on the first side of the lower layer.

21. The wound treatment apparatus of claim 1, wherein the absorbent layer comprises a first wound facing surface and an opposite second surface and wherein the three-dimensional filter comprises a first wound facing surface and an opposite second surface, wherein the three-dimensional filter comprises a first foldable flap coupled to the first wound facing surface of the three-dimensional filter and a second foldable flap coupled to the second surface of the three-dimensional filter, wherein the first foldable flap is located on a first surface of the absorbent layer and the second foldable flap is located on a second surface of the absorbent layer, and wherein the three-dimensional filter extends vertically through the recess of the absorbent layer.

22. The wound treatment apparatus of claim 10, wherein the absorbent layer comprises a first wound facing surface and an opposite second surface and wherein the three-dimensional filter comprises a first wound facing surface and an opposite second surface, wherein the three-dimensional filter comprises a first foldable flap coupled to the first wound facing surface of the three-dimensional filter and a second foldable flap coupled to the second surface of the three-dimensional filter, wherein the first foldable flap is located on a first surface of the absorbent layer and the second foldable flap is located on a second surface of the absorbent layer, and wherein the three-dimensional filter extends vertically through the recess of the absorbent layer.

* * * * *